(12) United States Patent
Gofman et al.

(10) Patent No.: US 10,503,876 B2
(45) Date of Patent: Dec. 10, 2019

(54) METHODS AND APPARATUS FOR ENHANCING A MEDICATION DELIVERY DEVICE

(71) Applicant: ASCENSIA DIABETES CARE HOLDINGS AG, Basel (CH)

(72) Inventors: Igor Y. Gofman, Croton-on-Hudson, NY (US); Jun Chen, Warren, NJ (US); James A. Johnson, Danbury, CT (US)

(73) Assignee: Ascensia Diabetes Care Holdings AG, Basel (CH)

( * ) Notice: Subject to any disclaimer, the term of this patent is extended or adjusted under 35 U.S.C. 154(b) by 328 days.

(21) Appl. No.: 15/125,143

(22) PCT Filed: Feb. 17, 2015

(86) PCT No.: PCT/US2015/016167
§ 371 (c)(1),
(2) Date: Sep. 10, 2016

(87) PCT Pub. No.: WO2015/138093
PCT Pub. Date: Sep. 17, 2015

(65) Prior Publication Data
US 2016/0378951 A1 Dec. 29, 2016

Related U.S. Application Data

(60) Provisional application No. 61/951,776, filed on Mar. 12, 2014.

(51) Int. Cl.
*G06F 19/00* (2018.01)
*A61M 5/315* (2006.01)
*A61M 5/20* (2006.01)

(52) U.S. Cl.
CPC ........... *G06F 19/3468* (2013.01); *A61M 5/20* (2013.01); *A61M 5/31528* (2013.01);
(Continued)

(58) Field of Classification Search
CPC ............ A61M 5/1723; A61M 5/31551; A61M 5/31535; A61M 5/20; A61M 5/31525;
(Continued)

(56) References Cited

U.S. PATENT DOCUMENTS

| 5,176,646 A | 1/1993 | Kuroda | |
| 6,482,185 B1 * | 11/2002 | Hartmann | A61M 5/31525 604/189 |

(Continued)

FOREIGN PATENT DOCUMENTS

| CN | 104245022 | 12/2014 |
| EP | 0810890 B1 | 11/2002 |

(Continued)

OTHER PUBLICATIONS

Tabbner's Nursing Care, theory and practice, Funnell et al. (Year: 2009).*

(Continued)

*Primary Examiner* — Manuel A Mendez
(74) *Attorney, Agent, or Firm* — Dugan & Dugan, PC

(57) ABSTRACT

Embodiments of the invention provide systems, methods, and apparatus for attaching an automated dose setting apparatus to a medication delivery device, receiving a first signal from an analyte monitoring system, the first signal indicating a dose of medication to be administered, and driving a dose knob of the medication delivery device with the automated dose setting apparatus to set a dose corresponding with the dose of medication to be administered. Numerous other aspects are disclosed.

20 Claims, 24 Drawing Sheets

(52) U.S. Cl.
CPC ..... *A61M 5/31546* (2013.01); *A61M 5/31551* (2013.01); *A61M 2205/18* (2013.01); *A61M 2205/35* (2013.01); *A61M 2205/3569* (2013.01); *A61M 2205/3584* (2013.01); *A61M 2205/3592* (2013.01); *A61M 2205/50* (2013.01); *A61M 2205/502* (2013.01); *A61M 2205/52* (2013.01); *A61M 2205/581* (2013.01); *A61M 2205/583* (2013.01); *A61M 2205/6072* (2013.01); *A61M 2209/01* (2013.01); *A61M 2230/005* (2013.01); *A61M 2230/201* (2013.01)

(58) Field of Classification Search
CPC .... A61M 5/31568; A61M 5/19; A61M 5/315; A61M 5/31585; A61M 5/24; A61M 5/14248; A61M 5/2033; A61M 5/31586; A61M 5/31553; G06F 19/3468
See application file for complete search history.

(56) References Cited

U.S. PATENT DOCUMENTS

| | | | |
|---|---|---|---|
| 8,333,739 | B2 | 12/2012 | Moller |
| 9,526,838 | B2 * | 12/2016 | Baran ................. A61M 5/24 |
| 10,052,435 | B2 | 8/2018 | Vouillamoz et al. |
| 2005/0192557 | A1 | 9/2005 | Brauker et al. |
| 2008/0306434 | A1 | 12/2008 | Dobbles et al. |
| 2008/0319384 | A1 | 12/2008 | Yodfat et al. |
| 2011/0009812 | A1 * | 1/2011 | Brown ................. A61B 5/155 604/31 |
| 2013/0245604 | A1 | 9/2013 | Kouyoumjian et al. |
| 2014/0276583 | A1 | 9/2014 | Chen et al. |

FOREIGN PATENT DOCUMENTS

| | | |
|---|---|---|
| EP | 0749332 B1 | 5/2005 |
| EP | 2572740 | 3/2013 |
| JP | 2007-525276 | 9/2007 |
| JP | 2013-544163 | 12/2013 |
| WO | WO 2005/082436 | 9/2005 |
| WO | WO 2010/092572 | 8/2010 |
| WO | WO 2012/072559 | 6/2012 |
| WO | WO 2013/065055 | 5/2013 |
| WO | WO 2013/114221 A2 | 8/2013 |
| WO | WO 2013/120778 | 8/2013 |
| WO | WO 2014/023763 | 2/2014 |
| WO | WO 2014/035672 A2 | 3/2014 |

OTHER PUBLICATIONS

Chinese Search Report of Chinese Application No. 201580024531.7 dated Dec. 24, 2018.

International Search Report and Written Opinion of International Application No. PCT/US15/16167 dated Oct. 28, 2015.

International Preliminary Report on Patentability of International Application No. PCT/US15/16167 dated Sep. 22, 2016.

* cited by examiner

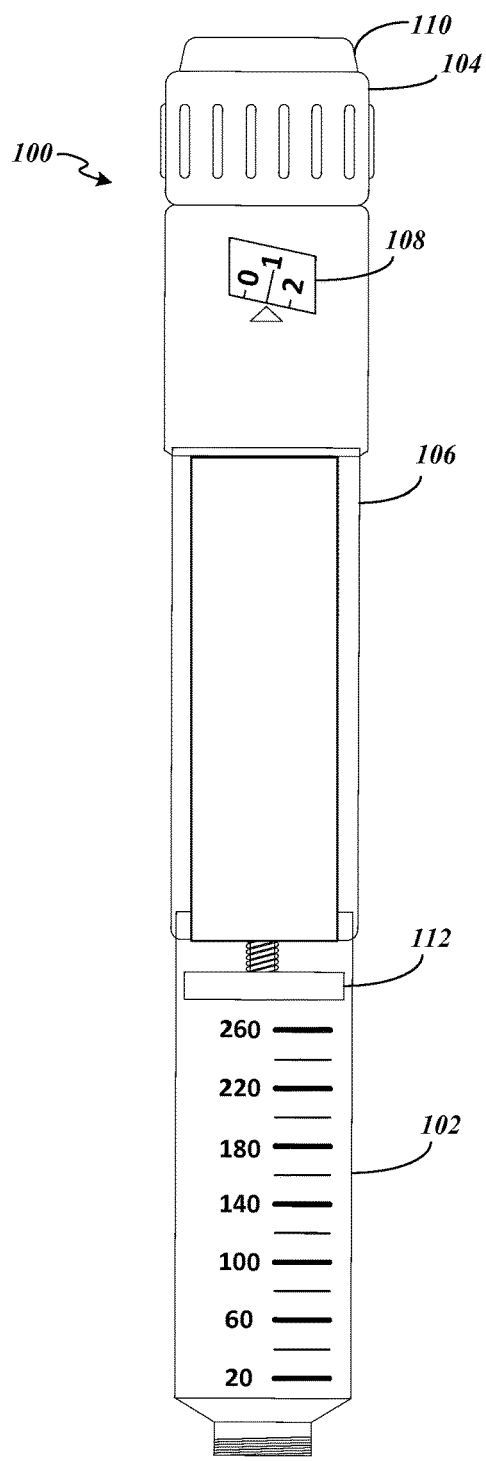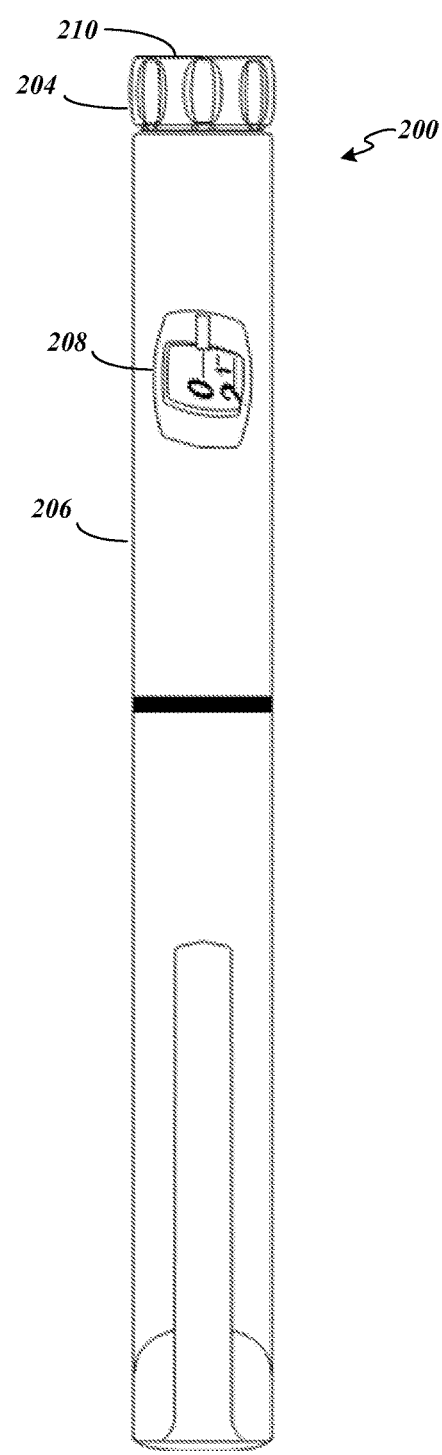
FIG. 1
(Prior Art)
FIG. 2
(Prior Art)

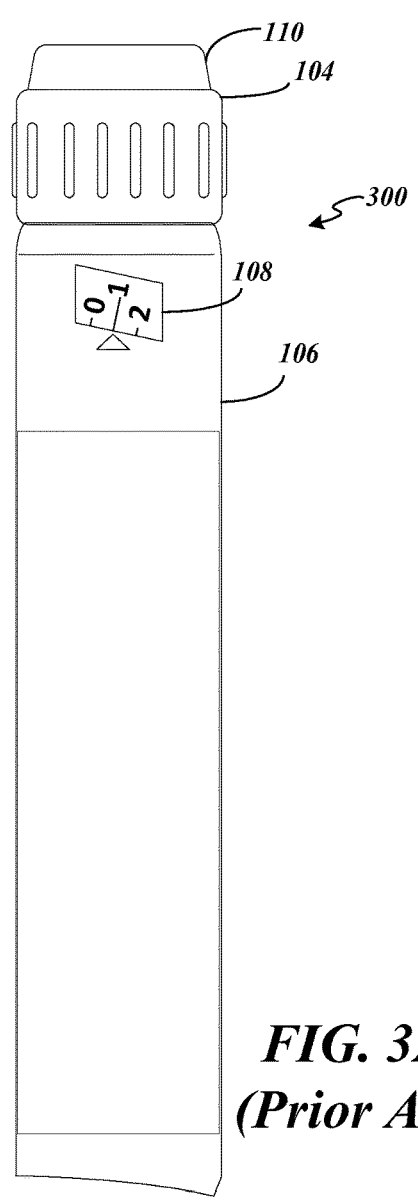
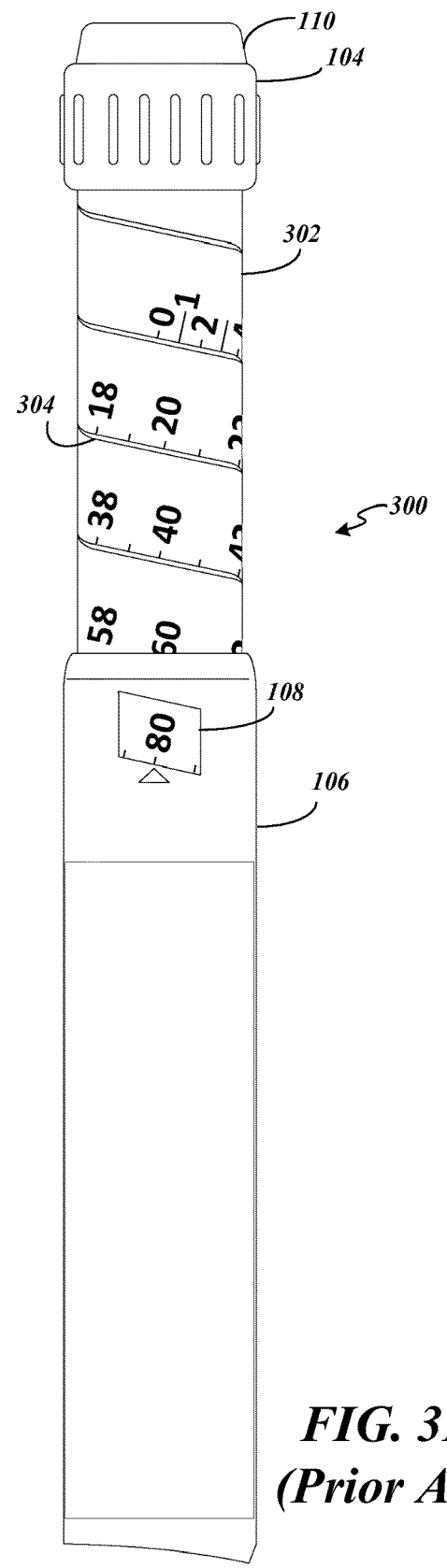
FIG. 3A
*(Prior Art)*
FIG. 3B
*(Prior Art)*

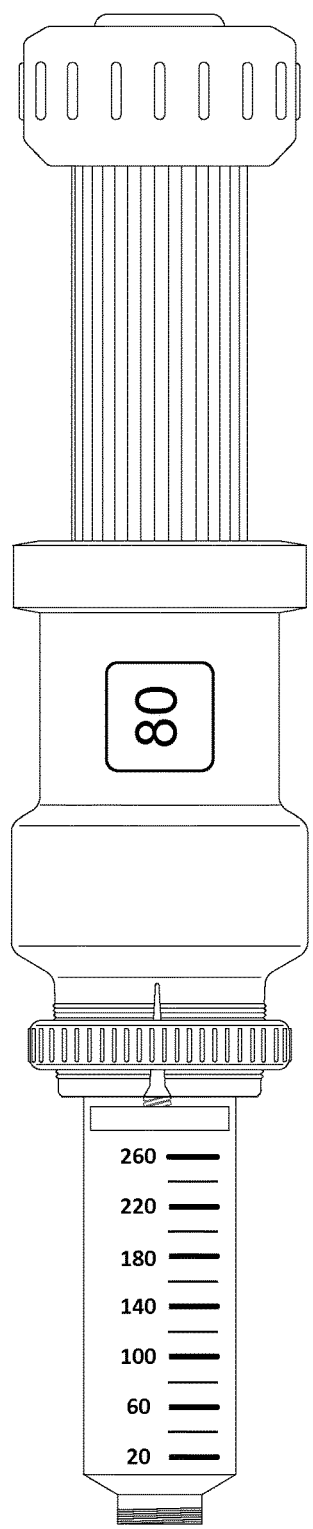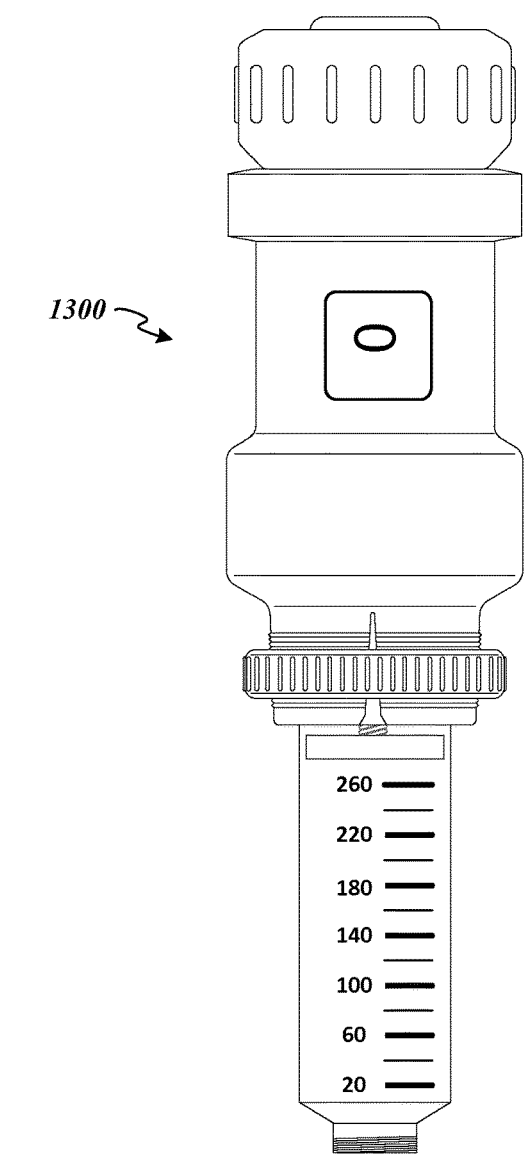
*FIG. 13A*
*FIG. 13B*

METHODS AND APPARATUS FOR ENHANCING A MEDICATION DELIVERY DEVICE

RELATED APPLICATIONS

The present application claims priority to U.S. Provisional Application No. 61/951,776 filed Mar. 12, 2014, and entitled "METHODS AND APPARATUS FOR ENHANCING A MEDICATION DELIVERY DEVICE", which is hereby incorporated by reference herein in its entirety for all purposes.

FIELD

The present invention relates to medication delivery devices, and more specifically to apparatus, systems, and methods for enhancement of such delivery devices.

BACKGROUND

Many different medication delivery devices and physiological fluid analyte monitoring systems are commercially available. A common application of such devices is the infusion of insulin to and the monitoring of blood glucose levels of diabetic patients. Increased portability and ease of use of such devices have enabled diabetic patients to administer a self-regulated medical treatment regime, which in turn provides an increased level of patient autonomy and privacy. This is particularly beneficial since diabetic patients' glucose levels may vary daily or hourly.

Such self-regulated diabetic treatment regimens often include the self-administration, either by injection and/or ingestion, of various medications, e.g., insulin. In addition to a high degree of medication compliance, for such self-regulated regimes to work effectively and safely, the patient is required to closely monitor the dosage and times at which medication is taken and may need to record or document corresponding medically relevant self-monitoring information, e.g., blood glucose level, insulin dosage, etc. The monitoring of such data helps to determine the current status and course of action (e.g., regimen change) of future actions. Because the recordation of this information can be time consuming and inconvenient, particularly if done with pen and paper, it is desirable that recordation, compilation and tracking of this type of information be minimized and time-efficient for the patient as possible.

Accordingly, there is continued interest in the development of improved devices and methods for the patient-regulated administration of medication and associated monitoring and recordation of medical information, including but not limited to drug administration (e.g., injection) time and dosage, analyte concentration (e.g., glucose levels, and the like). Of particular interest would be the development of a patient-controlled medication administration and monitoring system which provides the patient with flexibility and control, increases convenience, privacy and ease of use for the patient, and enhances portability of system components. Thus, what are needed are systems, apparatus, and methods for enhancing medication delivery devices.

SUMMARY

In some aspects, embodiments of the present invention provide an apparatus for automatically setting a dosage of a medication delivery device. The apparatus includes a first portion coupleable to a dose knob of a medication delivery device; and a second portion coupleable to a housing of the medication delivery device. The second portion is operable to receive dose information and to drive the first portion to set a dosage of the medication delivery device.

In other aspects, embodiments of the present invention provide a method for automatically setting a dosage of a medication delivery device. The method includes attaching an automated dose setting apparatus to a medication delivery device; receiving a first signal from an analyte monitoring system, the first signal indicating a dose of medication to be administered; and driving a dose knob of the medication delivery device with the automated dose setting apparatus to set a dose corresponding with the dose of medication to be administered.

In yet other aspects, embodiments of the present invention provide an apparatus for automatically monitoring a dosage of a medication delivery device. The apparatus includes a first portion coupleable to a dose knob of a medication delivery device; and a second portion coupleable to a housing of the medication delivery device. The second portion is operable to monitor movement of the first portion and to transmit a signal indicative of a dose of medication administered with the medication delivery device.

Numerous other aspects are provided in accordance with these and other embodiments of the invention. Other features and aspects of embodiments of the present invention will become more fully apparent from the following detailed description, the appended claims, and the accompanying drawings.

BRIEF DESCRIPTION OF THE DRAWINGS

FIG. 1 depicts an example of a disposable medication delivery device according to the prior art.

FIG. 2 depicts an example of a durable medication delivery device according to the prior art.

FIG. 3A depicts an example of a dosing stem of a medication delivery device in a retracted position according to the prior art.

FIG. 3B depicts an example of a dosing stem of a medication delivery device in a fully extended position according to the prior art.

FIG. 13A depicts a view of an example embodiment of a fully assembled automated dose setting apparatus in the extended position coupled to the medication delivery device of FIG. 1 according to some embodiments of the present invention.

FIG. 13B depicts a view of an example embodiment of a fully assembled automated dose setting apparatus in the retracted position coupled to the medication delivery device of FIG. 1 according to some embodiments of the present invention.

DETAILED DESCRIPTION

Figure 4:
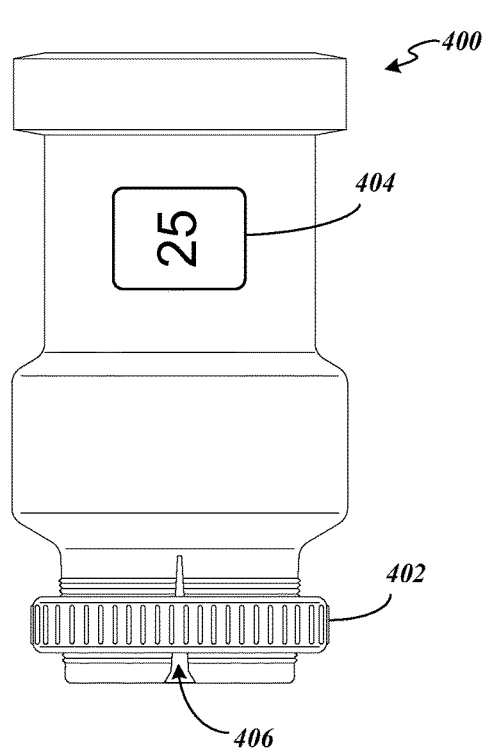
FIG. 4 depicts an example embodiment of a lower case of an automated dose setting apparatus according to some embodiments of the present invention.

Embodiments of the present invention provide enhancements to medication delivery devices intended to be used by patients for self-administration of medication (e.g., insulin). In some embodiments, an automated dose setting apparatus is provided that is adapted to be attached to any conventional pen-type medication delivery device. The automated dose setting apparatus includes a controller adapted to receive a signal (e.g., wirelessly) from an analyte monitoring system (e.g., a blood glucose monitor) or other health data manager device (e.g., smart phone, tablet, PC, wrist computer, etc.) that specifies an appropriate medication dose to administer. The controller is further operative to control an actuator apparatus to automatically set the dose of the medication delivery device. Thus, the automated dose setting apparatus provides an enhancement attachment that can be added to existing pen-type medication delivery devices.

In some other embodiments, an automated dose monitoring apparatus is provided that is adapted to be attached to any conventional pen-type medication delivery device. The automated dose monitor apparatus includes a controller adapted to receive a signal from one or more sensors coupled to the pen-type medication delivery device and to track the amount of medication that has been administered using the delivery device. The controller is further adapted to transmit a signal (e.g., wirelessly) that indicates the amount of medication that was actually administered along with a time and date of the administration. The signal is transmitted to an analyte monitoring system (e.g., a blood glucose monitor) or other health data manager device (e.g., smart phone, tablet, PC, wrist computer, etc.). Thus, the automated dose monitoring apparatus provides an enhancement attachment that can be added to existing pen-type medication delivery devices. In yet other embodiments, the principles of the invention can be applied to other types of medication delivery devices.

Turning now to FIGS. 1 and 2, examples of conventional pen-type medication delivery devices 100, 200 are shown. FIG. 1 depicts an unmodified disposable medication delivery device 100 similar to the Lantus® SoloSTAR® Pen manufactured by Sanofi-aventis U.S. LLC of Bridgewater, N.J., USA. FIG. 2 depicts an unmodified durable (e.g., reusable) medication delivery device 200 similar to the NovoPen® 4 manufactured by Novo Nordisk A/S of Alle, Denmark. Embodiments of the present invention can be coupled to either of these two medication delivery devices 100, 200, as well as others, without modification of the devices.

The pen-type medication delivery devices 100, 200 include a medication reservoir 102 where the unused medication is stored. The unused medication is injected into a patient through a detachable needle (not shown). The patient adjusts the dose knob 104, 204 by twisting the dose knob 104, 204 relative to the housing 106, 206 until an indication of the desired medication dose appears in the dose window 108, 208. As shown in FIGS. 3A and 3B, as the dose knob 104, 204 is twisted, the dose knob 104, 204 extends away from the housing 106, 206 revealing a dose stem 302 with dose markings 304. The dose stem 302 continues to extend until the patient has set the desired dose. The patient then can inject the medication by holding down the injection button 110, 210 at the top of the dose knob 104, 204. As the patient holds down the injection button 110, 210, the dose stem 302 retracts into the housing 106, 206 and causes a plunger 112 at the top of the medication reservoir 102 to compress the medication through the needle (not shown). Thus, the dose stem 302 of medication delivery device 300 in FIG. 3A is retracted into the housing 106 and thus, is not visible except through the dose window 108. The dose stem 302 in the delivery device 300 of FIG. 3B is extended and the dose markings 304 can be seen spiraling around the dose stem 302.

When patients use conventional medication delivery devices 100, 200 with retractable dose stems 302, the patients must manually turn the dose knob 104, 204 to set the dose. In addition, after administering the medication, the patients must manually enter the dose information into their analyte measurement meter (or other compliance tracking device). The potential for error is significant and the consequences of errors can endanger the health of the patient.

Figure 5:
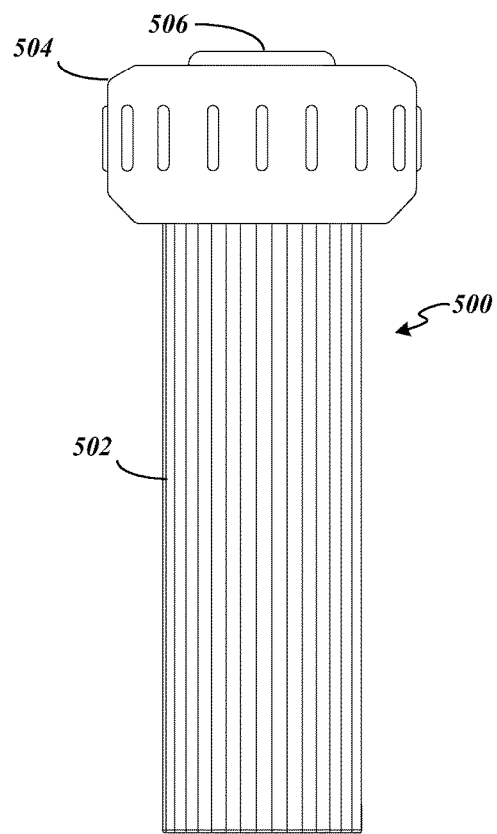
FIG. 5 depicts an example embodiment of an upper case of an automated dose setting apparatus according to some embodiments of the present invention.

Embodiments of the present invention avoid these potential errors by automating dose setting. FIG. 4 depicts a lower case 400 and FIG. 5 depicts an upper case 500 of an automated dose setting apparatus according to embodiments of the inventions. The lower case 400 and upper case 500 are attached to a conventional medication delivery device 100, 200 so that an analyte measurement system or other device can communicate a correct dose to the automated dose setting apparatus which in turn sets the dose to be administered without the patient having to determine the dose or turn the knob the correct number of turns.

The lower case 400 includes a compression fitting 402 that allows the lower case 400 to be securely fastened to the housing 106, 206 of the medication delivery device 100, 200. The compression fitting is adapted to securely couple to a wide range of medication devices including devices having a housing outer diameter of approximately 15 mm to approximately 25 mm. In some embodiments, other diameters can be accommodated with larger or smaller compression fittings and/or adapters. In other embodiments, different arrangements can be used to couple the lower case 400 to the medication delivery device 100, 200.

The lower case 400 also includes a display 404 for providing an indication of the dose set by the automated dose setting apparatus. As will be described in detail below, the lower case 400 houses a controller and associated electronics (e.g., memory, wiring, transceiver, sensors, etc.) adapted to operate the display 404 to indicate the dose.

The upper case 500 includes a cylinder shaft 502 with tooth fluting that is adapted to go over the dosing stem and rotatably couple to the lower case 400. The upper case 500 further includes a knob cover 504 that is adapted to securely couple to the dose knob 104, 204 of the medication delivery device 100, 200 using a gasket. In some embodiments, the knob cover 504 can include an opening to allow access to the injection button 110, 210 and in other embodiments, the knob cover 504 can include an extension button 506 that contacts and actuates the injection button 110, 210 when depressed.

Figure 6A:
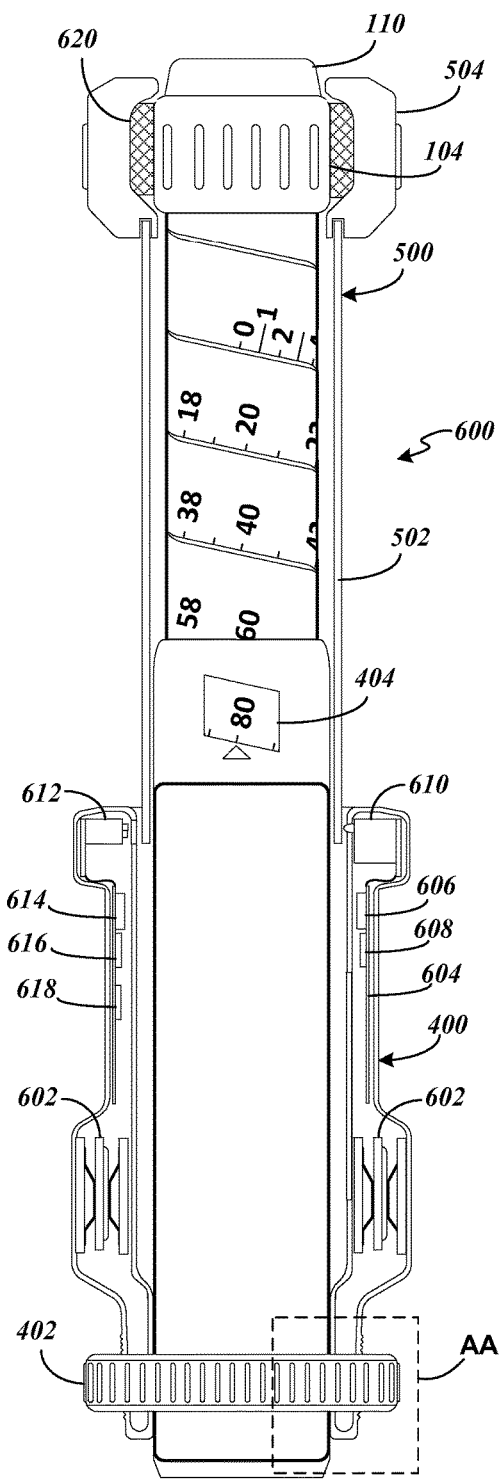
FIG. 6A depicts a cross-sectional view of an example embodiment of an automated dose setting apparatus according to some embodiments of the present invention.
Figure 6B:
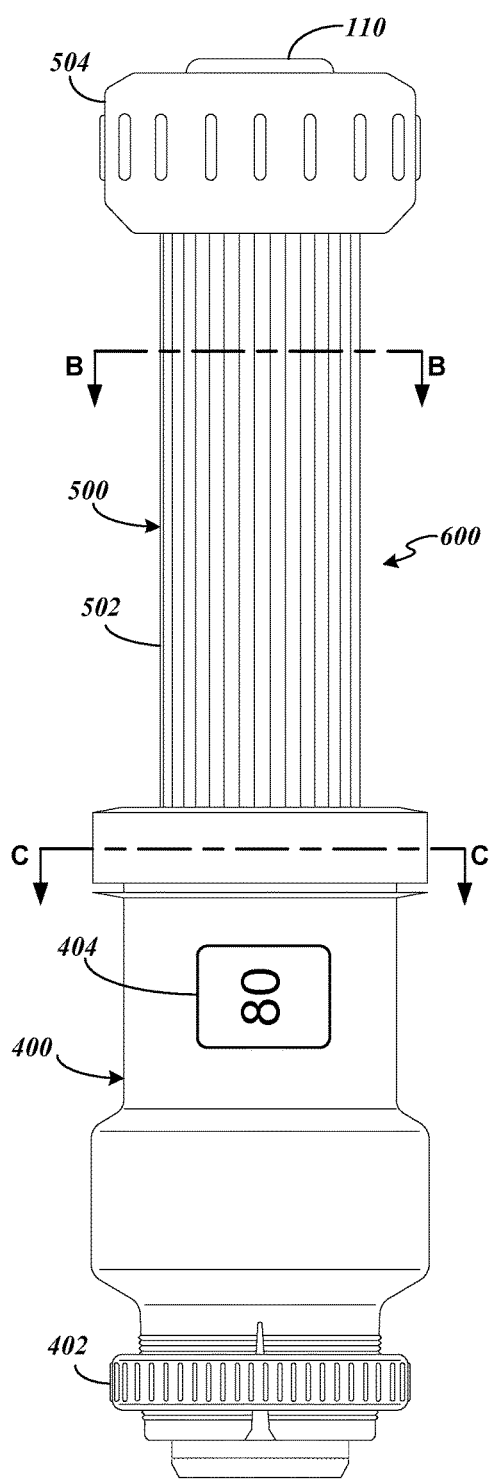
FIG. 6B depicts a side view of an example embodiment of an automated dose setting apparatus according to some embodiments of the present invention.

FIGS. 6A and 6B depict a cross-sectional view and a side view, respectively, of the assembled automated dose setting apparatus 600 including the lower case 400 rotatably coupled to the upper case 500. As can be seen most clearly in FIG. 6A, the lower case 400 can house a power supply 602 (e.g., one or more batteries) and an electronic circuit 604 (e.g., on a flexible circuit board that conforms to the inner diameter of the lower case 400) that can include a controller 606 (e.g., a microcontroller with memory 608), a driver assembly 610 (e.g., a Piezo stepper motor), a sensor assembly 612 (e.g., one or more capacitive/optical/magnetic position sensors), and a transceiver 614 (e.g., a radio frequency (RF) receiver/transmitter module). Other devices can also be included in the circuit 604 such as a clock generator 616 (e.g., an oscillator), a time and date clock module, and display driver circuitry 618 (e.g., to drive the display 404).

The upper case 500 includes the cylinder shaft 502 which is adapted to both be rotatably driven by the driver assembly 610 in the lower case 400 and to be position monitored by the sensor 612 which is also in the lower case 400. The upper case 500 can be made from aluminum and/or hard plastic. Other materials can be used.

Also visible in the cross-sectional view of FIG. 6A, within the knob cover 504 of the upper case 500, a gasket 620 is provided to secure the upper case 500 to the dose knob 104 of the medication delivery device 100, 200. Thus, cylinder shaft 502 which is attached to the knob cover 504 which is coupled to the dose knob 104 via gasket 620, is linked to the dose knob 104. In some embodiments, the gasket 620 can be made from rubber or similar material. Other materials can be used for the gasket 620 and various alternative methods can be used to secure the knob cover 504 to the dose knob 104.

In operation, electronic circuit 604 is adapted to track the rotational movement of the cylinder shaft 502 as the dose stem 302 is extended and/or retracted. As the teeth on the surface of the cylinder shaft 502 move past the sensor 612, the controller 606 can track the dosage setting or administration of the medication delivery device 100, 200. Using the transceiver 614, in some embodiments, the controller 606 can receive information (e.g., via a wireless signal from an analyte measurement system or other health data manager device (e.g., smart phone, tablet, PC, wrist computer, etc.)) indicating an intended dosage to be next administered. As will be described in detail below with respect to FIGS. 12A through 12C, the controller 606 can use the driver assembly 610 to automatically set the medication delivery device 100, 200 to the intended dosage based on the received information.

The controller 606 can further provide a confirmation indication to the patient (e.g., via status LEDs or audio tones) that the amount set to be administered is correct or an alarm if the amount set to be administered is different than the intended amount (e.g., in an error condition). Likewise, the controller 606 can provide a confirmation indication to the patient (e.g., via status LEDs or audio tones) if the amount actually administered is correct or an alarm if the amount actually administered is different than the intended amount. In addition, using the transceiver 614, in some embodiments, the controller 606 can wirelessly transmit a signal to an analyte measurement system or other health data manager device (e.g., smart phone, tablet, PC, wrist computer, etc.) that indicates the amount of medication that was administered using the medication delivery device coupled to the automated dose setting apparatus 600. In some embodiments, a time and date of the administration can also be transmitted.

Figure 7:
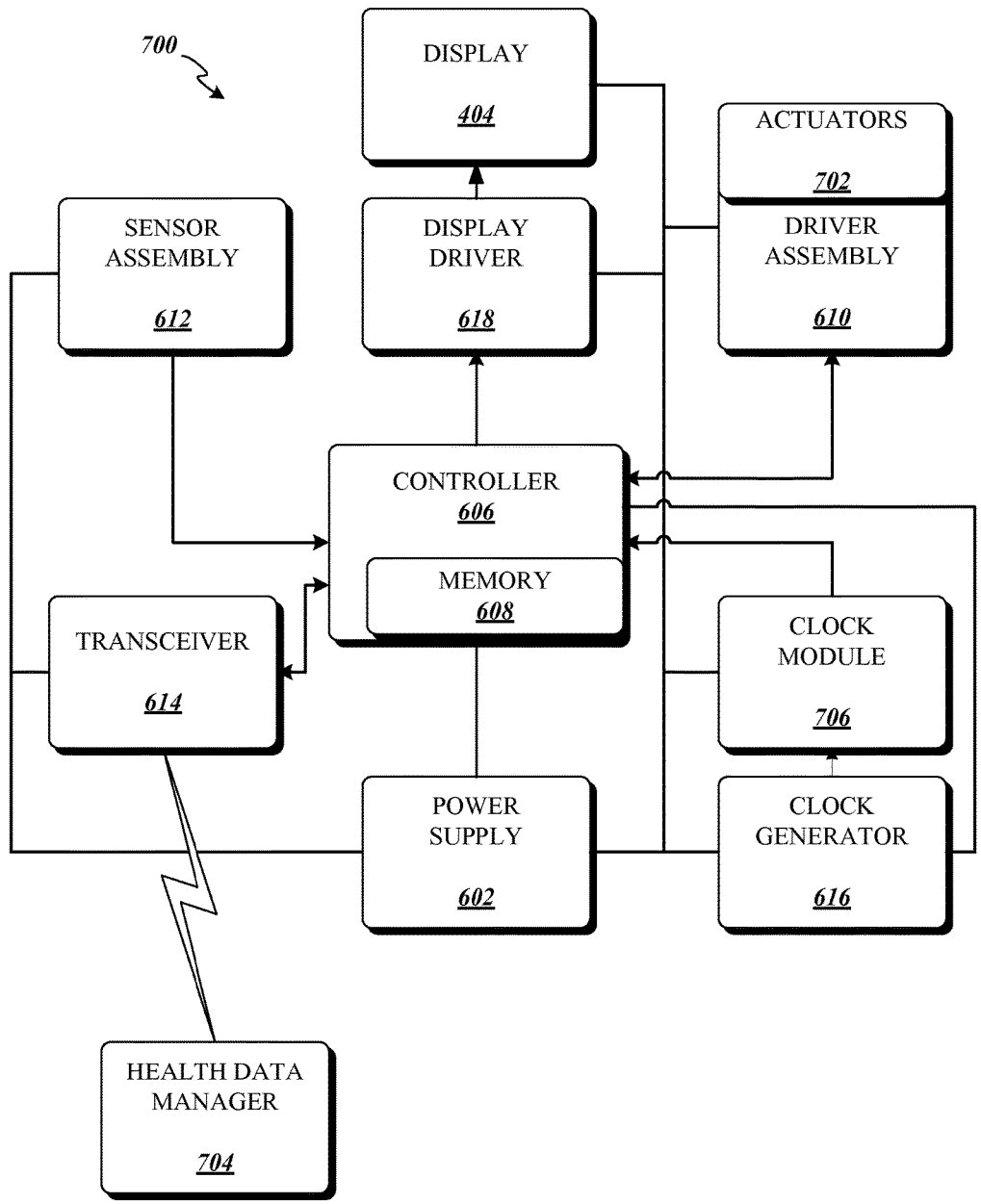
FIG. 7 depicts a block diagram of an example system architecture for an automated dose setting apparatus according to some embodiments of the present invention.

FIG. 7 is a block diagram depicting an example system architecture 700 for some embodiments of the automated dose setting apparatus 600. The system architecture 700 can include the controller 606 (e.g., a microcontroller with memory 608) that executes program instructions stored in the memory 608 to perform various methods of the present invention. Coupled to the controller 606, the system architecture 700 can further include the power supply 602 (e.g., one or more batteries), the driver assembly 610 (e.g., a Piezo stepper motor) including actuators 702, the sensor assembly 612 (e.g., including one or more capacitive/optical/magnetic sensors for tracking knob/shaft position and/or reading other encoded markings on the cylinder shaft 502, FIG. 5), and the transceiver 614 (e.g., a radio frequency (RF) receiver/transmitter module) for wireless communication with a health data manager device 704 (e.g., an analyte measurement system or health data manager software running on a smart phone, tablet, PC, wrist computer, etc.). Other devices can also be coupled to the controller 606 such as the clock generator 616 (e.g., an oscillator), a time and date clock module 706, and the display driver circuitry 618 to drive the display 404. In addition to the controller 606, the power supply can be coupled to the driver assembly 610, the sensor assembly 612, the transceiver 614, the clock generator 616, the time and date clock module 706, the display driver circuitry 618, and the display 404.

Figure 8:
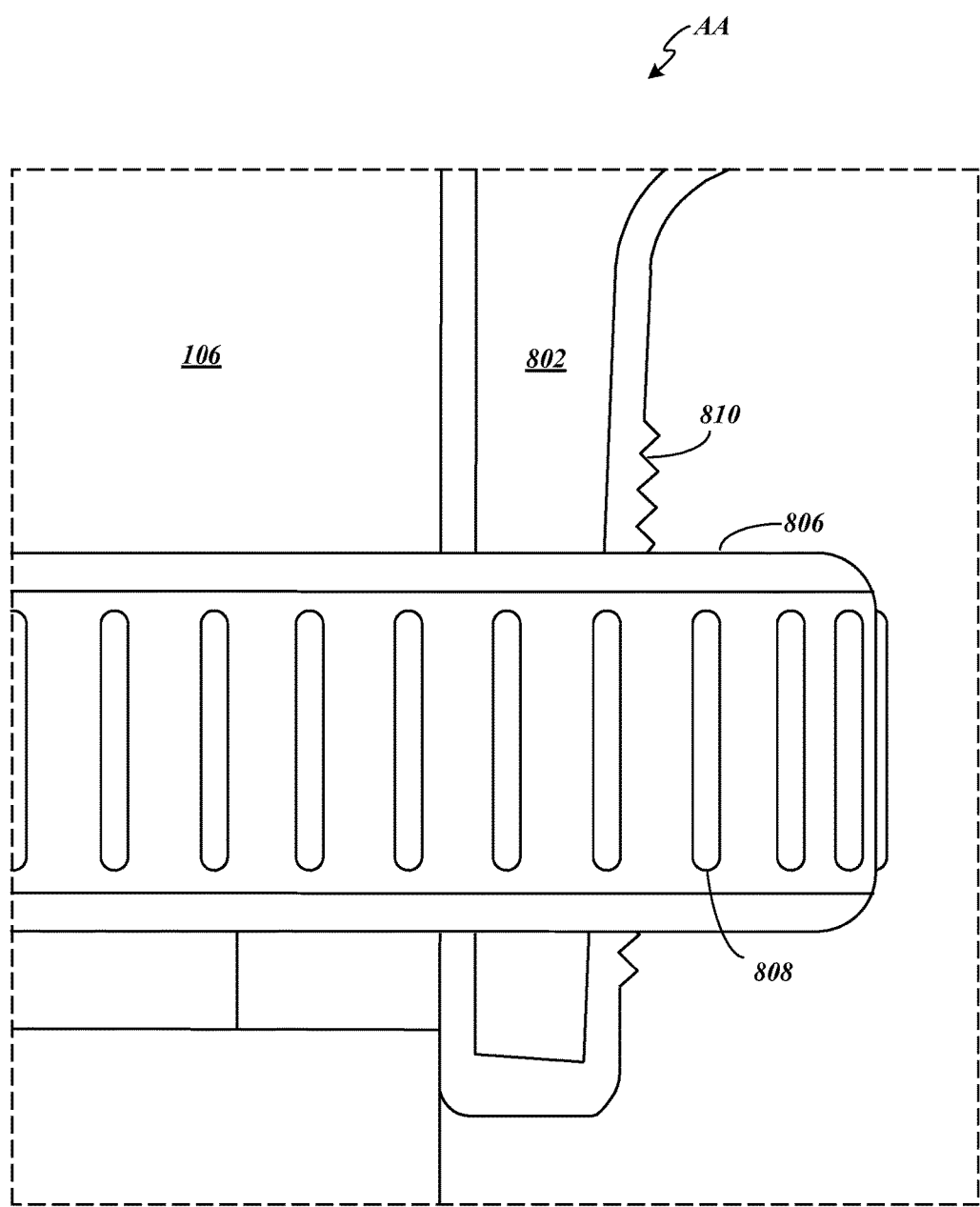
FIG. 8 depicts a magnified view of the portion surrounded by dashed lines and labeled AA in FIG. 6A.

FIG. 8 depicts details of the compression fitting 402 for securing the lower case 400 to the housing 106 of the medication delivery device 100 by illustrating a magnified view of the area surrounded by the dashed lines labeled AA in FIG. 6A. A flexible, hollow, threaded cone 802 is provided at the base of the lower case 400 including a gap (not shown in FIG. 8 but see 406 of FIG. 4). The threaded cone 802 is placed around the housing 106 of the medication delivery device 100 and a compression nut 806 including ridges 808 for grip is screwed onto the threaded cone 802. As the threaded cone 802 extends up along the lower case 400, the threads 810 increase in diameter and in response to the compression nut 806 being tightened, the threaded cone 802 is compressed and constricted around the housing 106, securing the lower case 400 to the housing 106 of the medication delivery device 100. In some embodiments, the lower case 400 including the threaded cone 802 is made from a semi-flexible material such as aluminum or polyethylene and the compression nut 806 is made from nylon or other hard plastic. Many other practicable materials can be used for these components.

Figure 9:
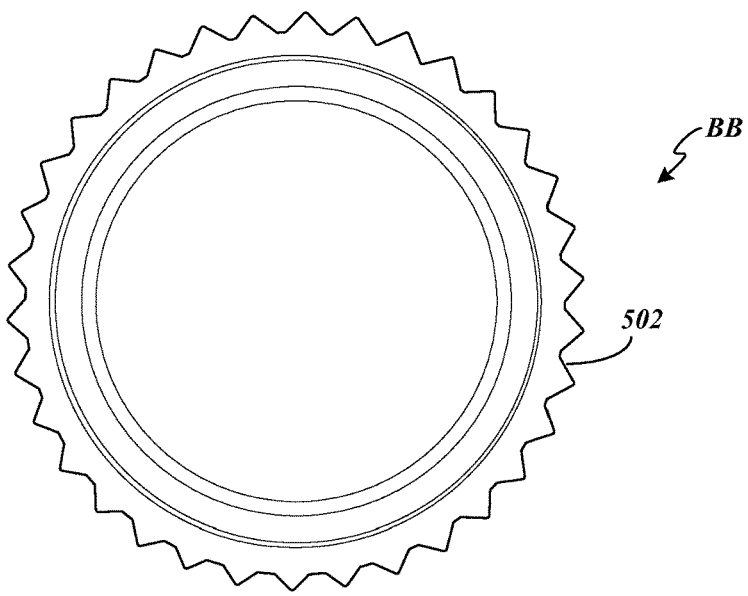
FIG. 9 depicts a cross-sectional view taken at cut line BB of FIG. 7.
Figure 10:
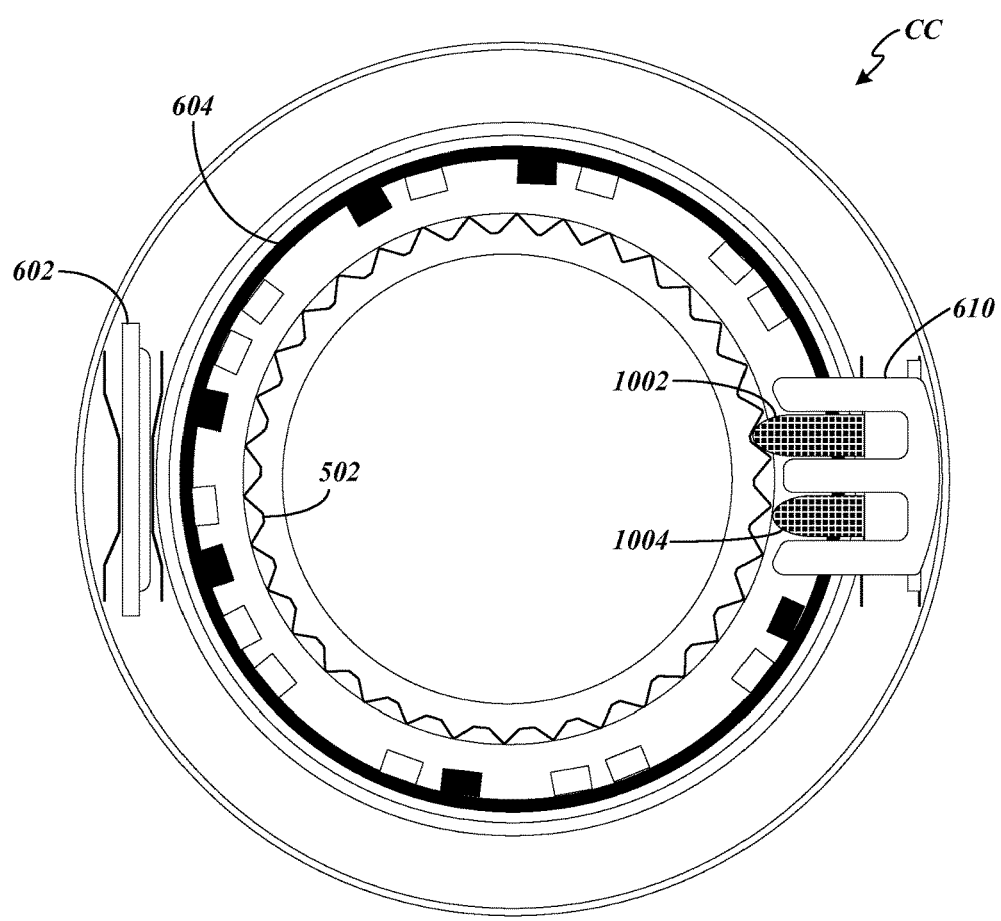
FIG. 10 depicts a cross-sectional view taken at cut line CC of FIG. 7.

FIG. 9 depicts a cross-sectional view of the upper case 500 taken at cut line BB of FIG. 7. Note that the tooth fluting of the cylinder shaft 502 gives the outer surface of the cylinder shaft 502 a gear-shaped cross-section. FIG. 10 depicts a cross-sectional view of the upper case 500 inserted into the lower case 400 taken at cut line CC of FIG. 7. This view illustrates the position of the driver assembly 610 relative to the cylinder shaft 502. As can be seen in FIG. 10, actuators 1002, 1004 within the driver assembly 610 are disposed to engage the tooth fluting of the cylinder shaft 502 to cause the cylinder shaft 502 to rotate. Operation of the driver assembly 610 is described in more detail below with respect to FIGS. 12A to 12C. Also shown in FIG. 10 are the power supply 602 and the electronic circuit 604.

Figure 11:
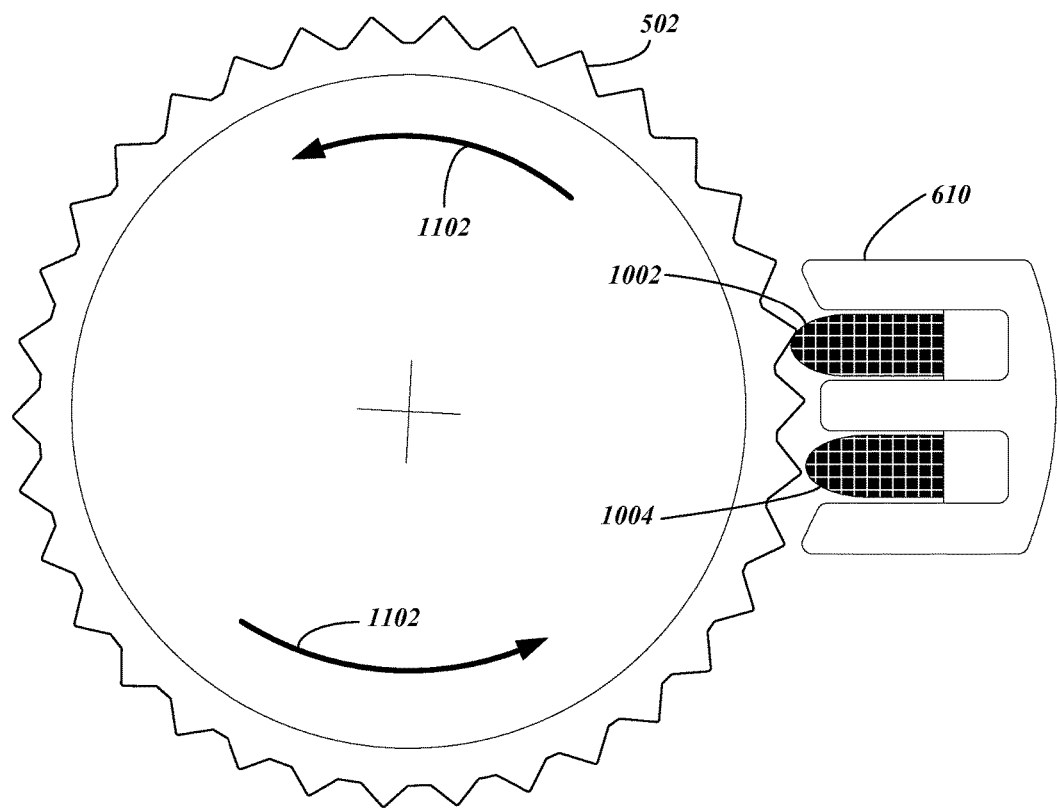
FIG. 11 depicts a magnified schematic representation of an example embodiment of the driver assembly depicted in the cross-sectional view of FIG. 10.

FIG. 11 depicts a magnified schematic representation of an example embodiment of the driver assembly 610 depicted in the cross-sectional view of FIG. 10. The actuators 1002, 1004 of the driver assembly 610 alternately press against the teeth of the outer surface of the cylinder shaft 502. These alternating linear forces are thus translated into rotational force to drive the cylinder shaft 502 to rotate about its longitudinal axis as indicated by arrows 1102. Note that the cylinder shaft 502 is coupled to the knob cover 504 (FIG. 6A) which is secured to the dose knob 104 (FIG. 6A). Thus, the driver assembly 610 is adapted to turn the dose knob 104 when the upper case 500 and lower case 400 are attached to a medication delivery device 100, 200. In some embodiments, the cylinder shaft 502 of the upper case 500 is made from a material such as aluminum or hard plastic and the actuators 1002, 1004 of the driver assembly 610 are made from piezoelectric material, such as, for example, barium titanate, lead titanate, lead zirconate titanate, potassium niobate, lithium niobate, lithium tantalite, or sodium tungstate. Many other practicable materials can be used for these components.

Figure 12A:
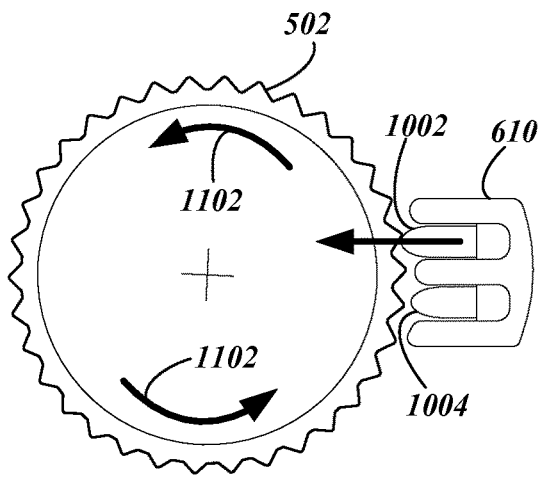
FIG. 12A to 12C depict an example of the operation of the driver assembly depicted in the cross-sectional view of FIG. 10.
Figure 12B:
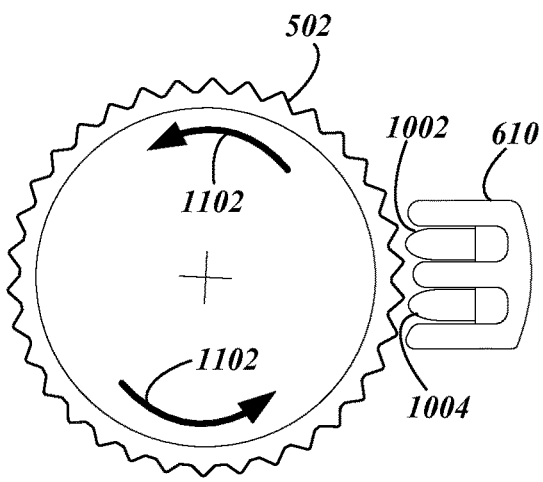
Figure 12C:
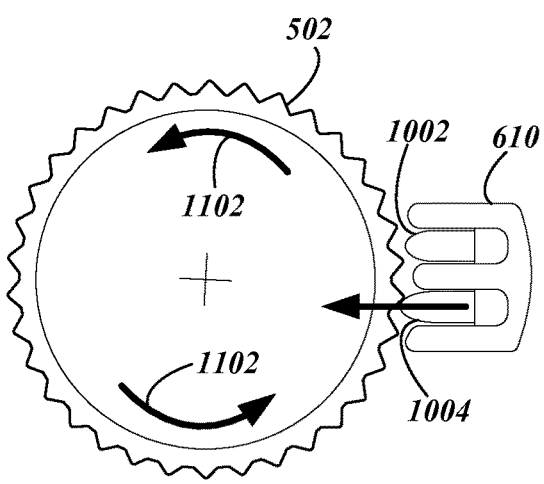

FIGS. 12A through 12C depict an example sequence of operation of the driver assembly 610. As described above, the driver assembly 610 can include two actuators 1002, 1004 that are controlled to activate sequentially. In some embodiments, a repeating sequence as represented by FIGS. 12A through 12C can be used to precisely turn the cylinder shaft 502 (and ultimately the dose knob 104, 204) to a desired position. Embodiments of the invention include the controller 606 receiving a signal indicating a desired dose (e.g., from an analyte monitoring system or other device) and determining how many repetitions of the sequence would be required to set the attached medication delivery device to the desired dose.

In FIG. 12A, an electrical signal from the controller 606 is applied to the first actuator 1002. The first actuator 1002 of the driver assembly 610, which can include a Piezo material, expands to push against a tooth of the cylinder shaft 502. The cylinder shaft 502 rotates in the direction of the arrow 1102 (e.g., counter-clockwise) a single "step" in response to the linear force from the first actuator 1002. In the second step, as depicted in FIG. 12B, the controller 606 removes the electrical signal from the first actuator 1002 and the first actuator 1002 contracts away from the cylinder shaft 502. Note that the first actuator 1002 contracts a sufficient amount to be clear of the teeth of the cylinder shaft 502.

In the third step of this example sequence, the controller 606 applies an electrical signal to the second actuator 1004. The second actuator 1004 thus expands and pushes against another tooth of the cylinder shaft 502. The cylinder shaft 502 rotates in the direction of the arrow 1102 (e.g., counter-clockwise) a single "step" in response to the linear force from the second actuator 1002. In the fourth step, not shown but would look the same as the depiction in FIG. 12B, the controller 606 removes the electrical signal from the second actuator 1004 and the second actuator 1004 contracts away from the cylinder shaft 502. Note that the second actuator 1004 contracts a sufficient amount to be clear of the teeth of the cylinder shaft 502.

This process can be repeated as many times as necessary to achieve the desired position of the dose knob 104, 204. Using the sensor 612 to detect movement of the cylinder shaft 502, the controller 606 is able to determine when the dose knob 104, 204 has been rotated the desired amount. In some embodiments, the controller 606 can be further adapted to cause the display 404 to provide an indication of the dose that has been set by the controller.

FIG. 13A depicts a view of an example embodiment of a fully assembled automated dose setting apparatus 1300 attached to a medication delivery device 100, 200 (FIGS. 1 and 2). The automated dose setting apparatus 1300 is shown in the extended position. FIG. 13B depicts a view of the example embodiment of a fully assembled automated dose setting apparatus 1300 attached to a medication delivery device 100, 200 (FIGS. 1 and 2). The automated dose setting apparatus 1300 is shown in the retracted position.

Figures 14, 15:
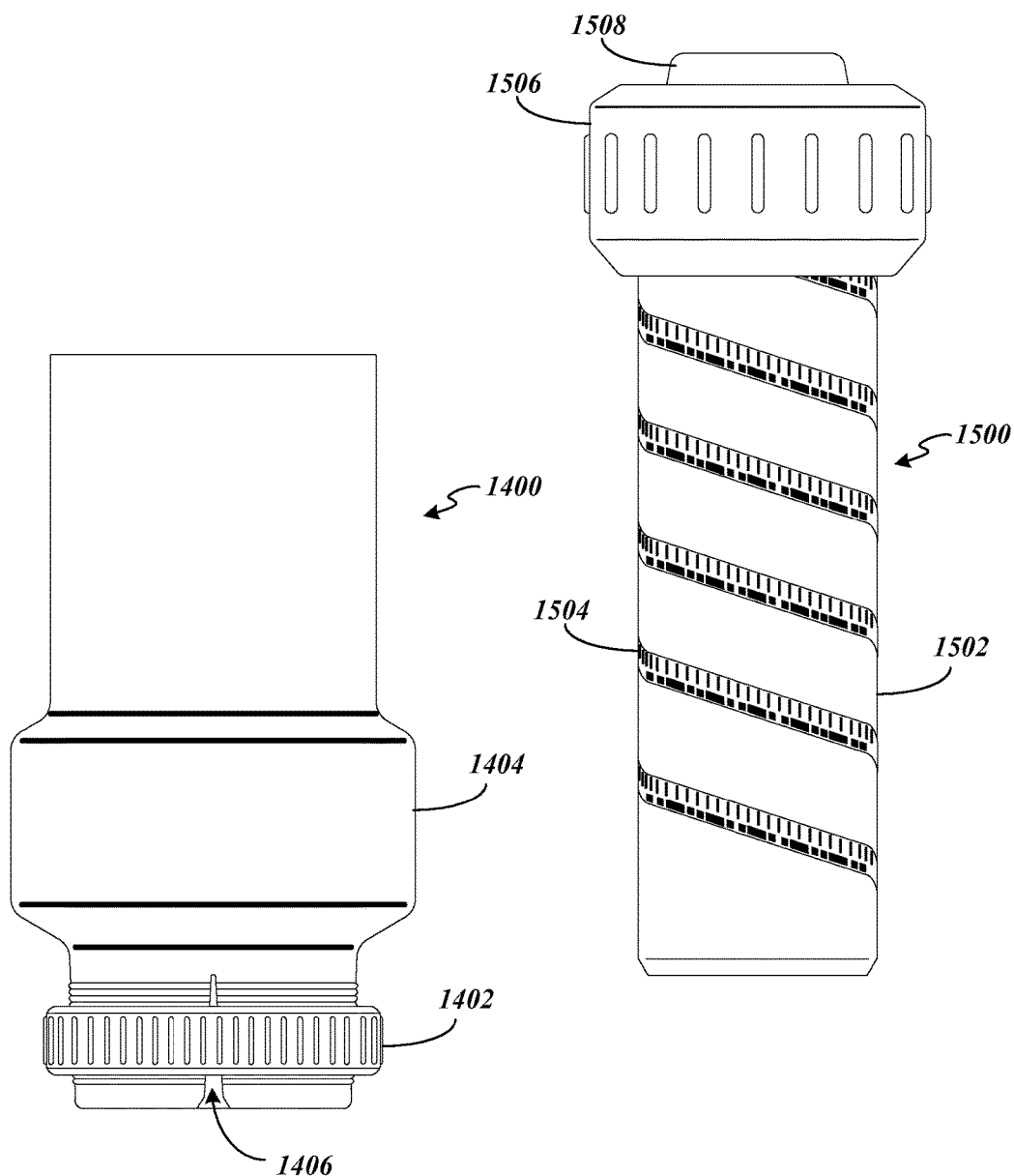
FIG. 14 depicts an example embodiment of a lower case of an automated dose monitoring apparatus according to some embodiments of the present invention.
FIG. 15 depicts an example embodiment of an upper case of an automated dose monitoring apparatus according to some embodiments of the present invention.
Figure 16:
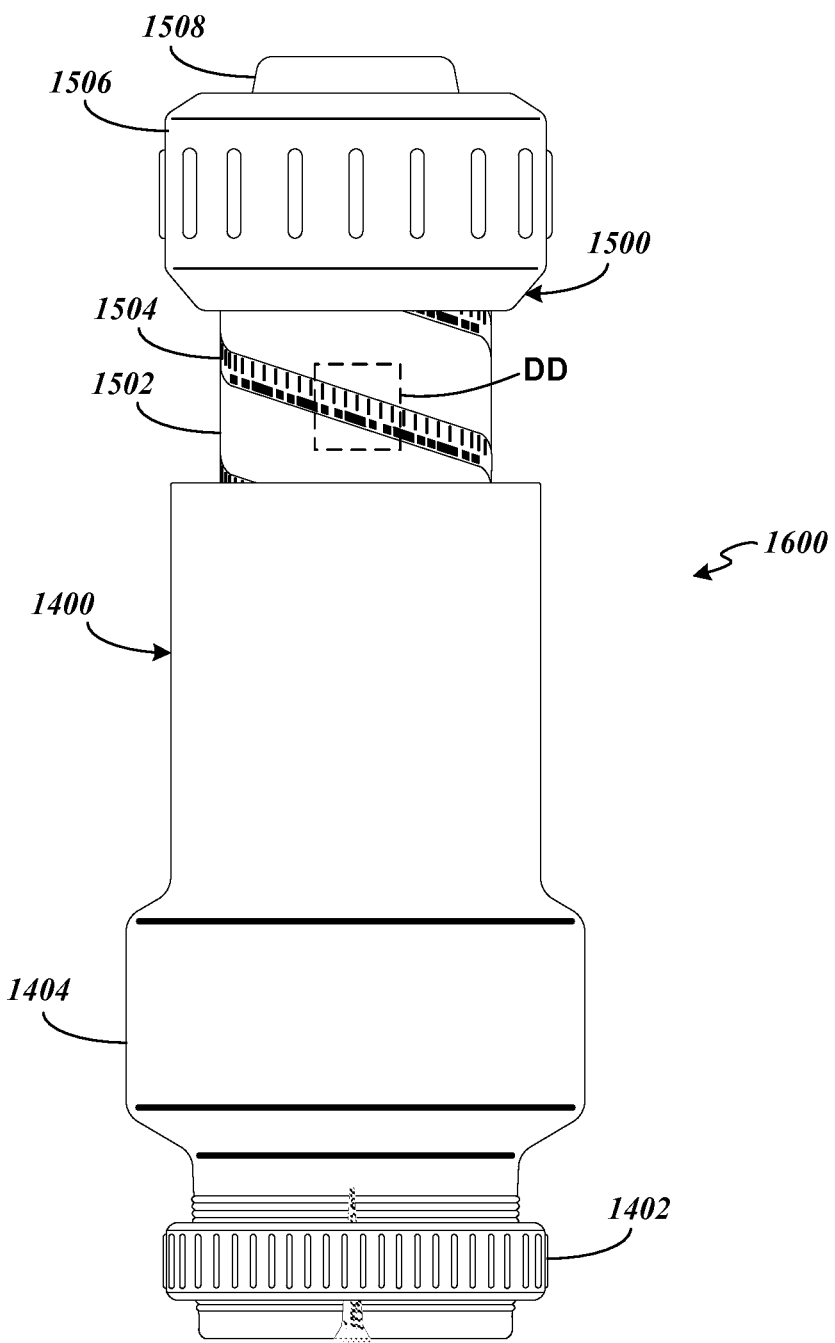
FIG. 16 depicts a side view of an example embodiment of an automated dose monitoring apparatus according to some embodiments of the present invention.

Turning now to FIGS. 14 to 16, an alternative embodiment of the present invention is described. In some embodiments, the invention provides an automated dose monitoring apparatus that is adapted to be attached to any conventional pen-type medication delivery device 100, 200. As with the automated dose setting apparatus 1300, an automated dose monitoring apparatus includes a lower case 1400 and an upper case 1500, both adapted to be attached to a medication delivery device 100, 200. FIG. 14 depicts an example embodiment of a lower case of an automated dose monitoring apparatus according to some embodiments of the present invention. The lower case 1400 includes a compression fitting 1402 that is similar to the compression fitting 402 of the lower case 400 of the automated dose setting apparatus 1300. The compression fitting 1402 enables secure attachment of the lower case 1400 to the housing 106, 206 of the medication delivery device 100, 200. The lower case 1400 also includes a body portion 1404 adapted to house and support electronics as will be discussed below.

FIG. 15 depicts an example embodiment of an upper case of an automated dose monitoring apparatus according to some embodiments of the present invention. The upper case 1500 includes a transparent (or semi-transparent) cylinder shaft 1502 that includes dosage indicator markings 1504 (e.g., a spiral bar code strip). The upper case 1500 also includes a knob cover 1506 and an extension button 1508 that contacts and actuates the injection button 110, 210 of the medication delivery device 100, 200 when the extension button 1508 is depressed. The knob cover 1506 includes features for securing the upper case 1500 to the dose knob 104, 204 of the medication delivery device 100, 200.

FIG. 16 depicts a side view of an example assembled automated dose monitoring apparatus 1600 according to some embodiments of the present invention. As shown the, the cylinder shaft 1502 of the upper case 1500 is inserted into and rotatably coupled to the body portion 1404 of the lower case 1400.

Figure 17:
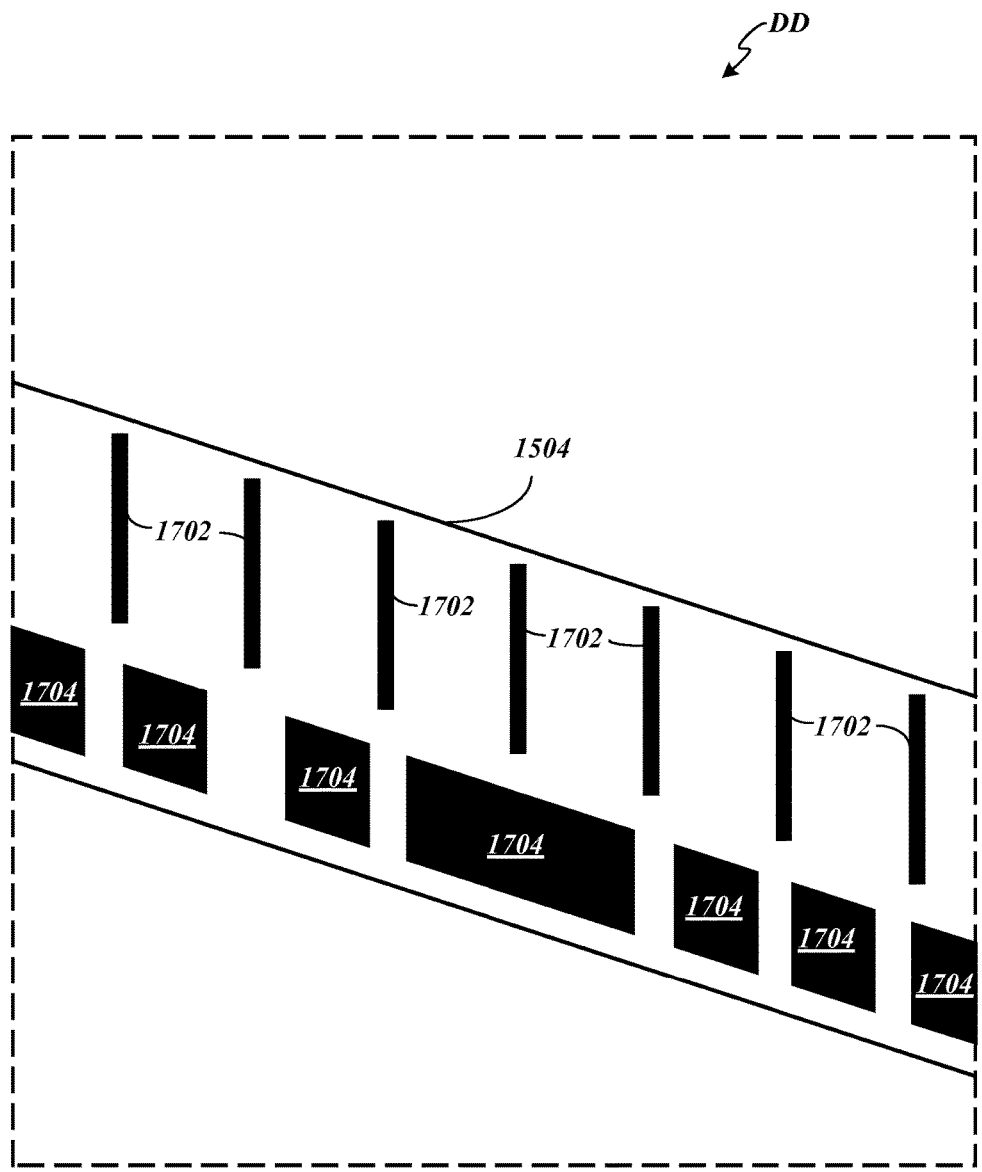
FIG. 17 depicts a magnified view of the portion surrounded by dashed lines and labeled DD in FIG. 16.

FIG. 17 depicts a magnified view of the portion of the dosage indicator markings 1504 surrounded by dashed lines and labeled DD in FIG. 16. In some embodiments, the dosage indicator markings 1504 can include two or more sets of indicators 1702, 1704. For example, in the embodiment shown, the indicator marks in the upper set of indicators 1702 are consistently spaced and can be used for position synchronization. These indicator marks are spaced to correspond to the dose markings 304 on the medication delivery device's dose stem 302 (FIG. 3B). A second set of indicators 1704 at the lower portion of the spiral dosage indicator markings 1504 can be used to provide an identifier code for medication type (e.g., insulin type). The cylinder shaft 1502 is detachable and can be unique for different size medication containers and can include unique sets of indicators for different medications and for each type of a given medication (e.g., insulin type 1, 2, 3, etc.).

Figure 18A:
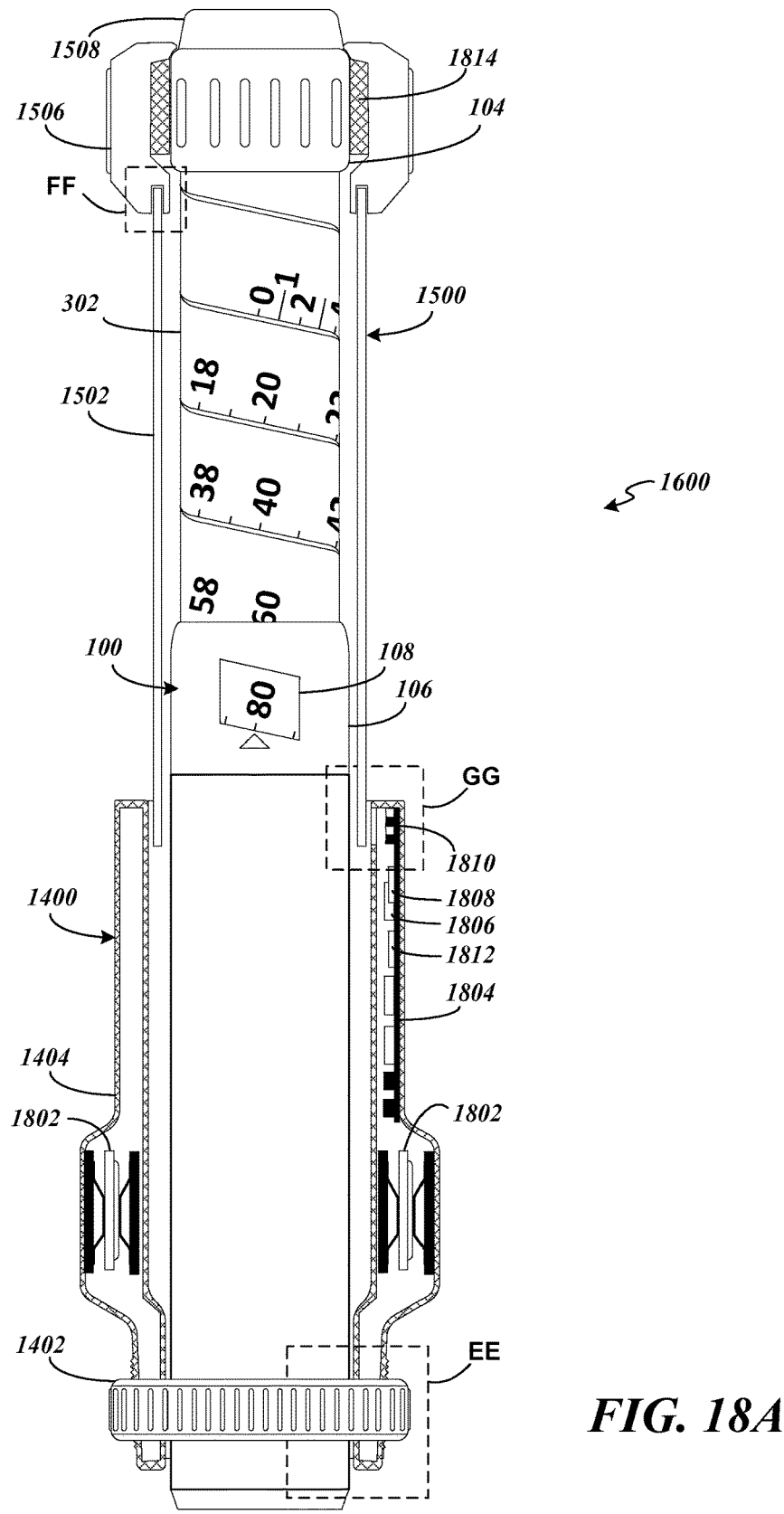
FIG. 18A depicts a cross-sectional view of an example embodiment of an automated dose monitoring apparatus attached to a medication delivery device with a fully extended dosing stem according to some embodiments of the present invention.
Figure 18B:
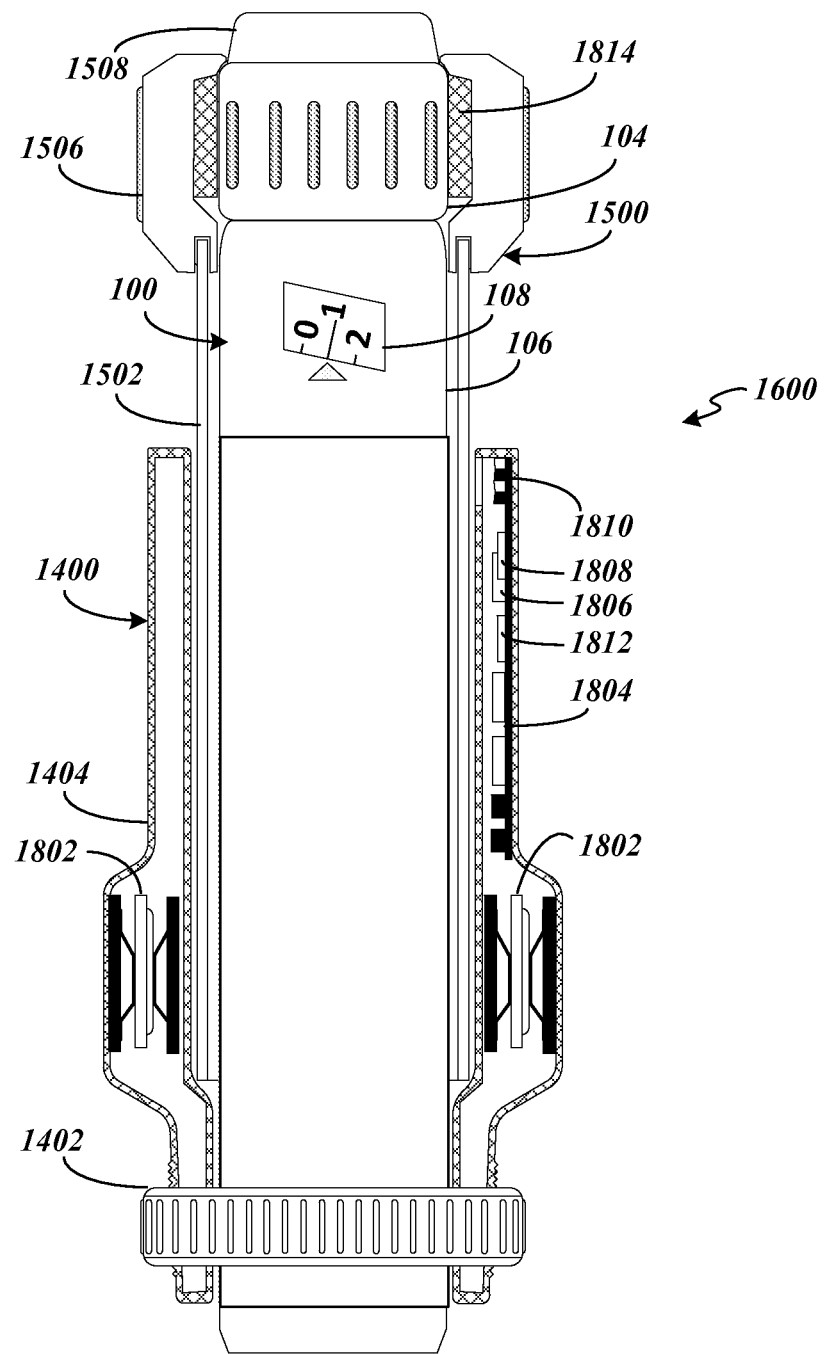
FIG. 18B depicts a cross-sectional view of an example embodiment of an automated dose monitoring apparatus attached to a medication delivery device with the dosing stem in a retracted position according to some embodiments of the present invention.

FIGS. 18A and 18B depict cross-sectional views of an example embodiment of an automated dose monitoring apparatus 1600 attached to a medication delivery device 100, 200. In FIG. 18A, the dosing stem 302 of the medication delivery device 100, 200 is fully extended and in FIG. 18B, the dosing stem 302 is fully retracted.

As can be seen most clearly in FIG. 18A, the lower case 1400 can house a power supply 1802 (e.g., one or more batteries) and an electronic circuit 1804 (e.g., on a flexible circuit board that conforms to the inner diameter of the lower case 1400) that can include a controller 1806 (e.g., a microcontroller with memory 1808), a sensor assembly 1810 (e.g., one or more capacitive/optical/magnetic sensors), and a transceiver 1812 (e.g., a radio frequency (RF) receiver/transmitter module). Additional devices can also be included in the circuit 1804 and coupled to the controller such as a clock generator (e.g., an oscillator), one or more status LEDs, a time and date clock module, and an audio output speaker.

In operation, electronic circuit 1804 is adapted to read the dosage indicator markings 1504 as the dose stem 302 is extended and/or retracted. As the dosage indicator markings 1504 move past the sensor assembly 1810, the controller 1806 can track the dosage setting of the medication delivery device. Using the transceiver 1812, in some embodiments, the controller 1806 can receive information (e.g., via a wireless signal from an analyte measurement system or other health data manager device (e.g., smart phone, tablet, PC, wrist computer, etc.)) indicating an intended dosage to be next administered. The controller 1806 can provide a confirmation indication to the patient (e.g., via status LEDs or audio tones) if the amount set to be administered is correct or an alarm if the amount set to be administered is different than the intended amount. Likewise, the controller 1806 can provide a confirmation indication to the patient (e.g., via status LEDs or audio tones) if the amount actually administered is correct or an alarm if the amount actually administered is different than the intended amount. In addition, using the transceiver 1812, in some embodiments, the controller 1806 can wirelessly transmit a signal to an analyte measurement system or other health data manager device (e.g., smart phone, tablet, PC, wrist computer, etc.) that indicates the amount of medication that was administered using the medication delivery device coupled to the automated dose monitoring apparatus 1600. In some embodiments, a time and date of the administration can also be transmitted.

Also visible in the cross-sectional view of FIG. 18A, within the knob cover 1506 of the upper case 1500, a gasket 1814 is provided to secure the upper case 1500 to the dose knob 104 of the medication delivery device 100, 200. In some embodiments, the gasket 1814 can be made from rubber or similar material. Other materials can be used for the gasket 1814 and various alternative methods can be used to secure the knob cover 1506 to the dose knob 104.

Figure 19:
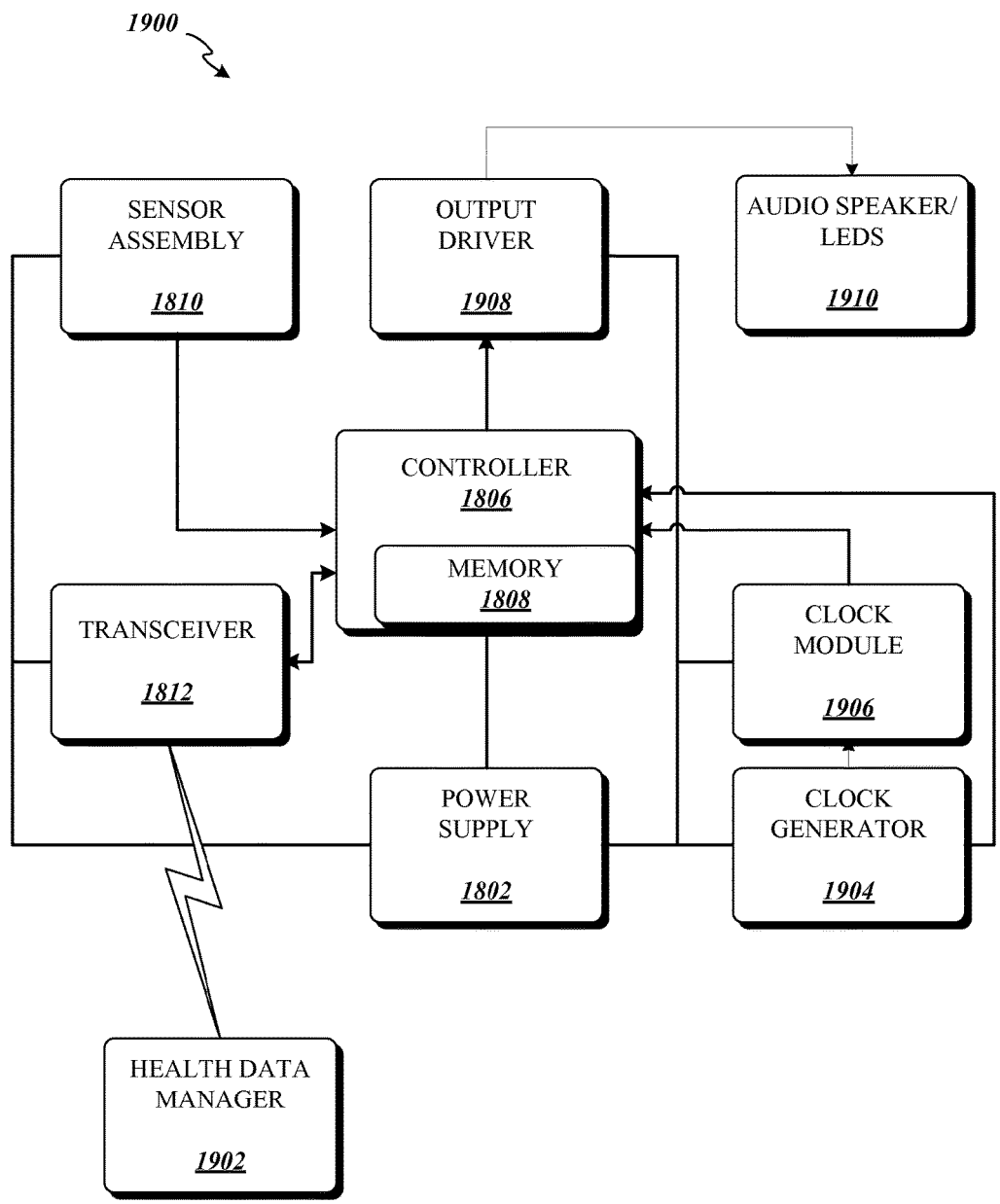
FIG. 19 depicts a block diagram of an example system architecture for an automated dose monitoring apparatus according to some embodiments of the present invention.

FIG. 19 is a block diagram depicting an example system architecture 1900 for some embodiments of the automated dose monitoring apparatus 1600. The system architecture 1900 can include the controller 1806 (e.g., a microcontroller with memory 1808) that executes program instructions stored in the memory 1808 to perform various methods of the present invention. Coupled to the controller 1806 (e.g., to send and/or receive control signals and/or data signals), the system architecture 1900 can further include the sensor assembly 1810 (e.g., including one or more capacitive/optical/magnetic sensors for tracking knob/shaft position and/or reading other encoded markings on the cylinder shaft 1502, FIG. 18A), and the transceiver 1812 (e.g., a radio frequency (RF) receiver/transmitter module) for wireless communication with a health data manager device 1902 (e.g., an analyte measurement system or health data manager software running on a smart phone, tablet, PC, wrist computer, etc.). Other devices can also be coupled to the controller 1806 to send and/or receive control signals and/or data signals such as the clock generator 1904 (e.g., an oscillator), a time and date clock module 1906, and the output driver 1908 to drive an audio speaker and/or status LEDs 1910. In addition to the controller 1806, the power supply 1802 (e.g., one or more batteries), can be coupled to the sensor assembly 1810, the transceiver 1812, the clock generator 1904, the time and date clock module 1906, and the output driver 1908.

Figure 20:
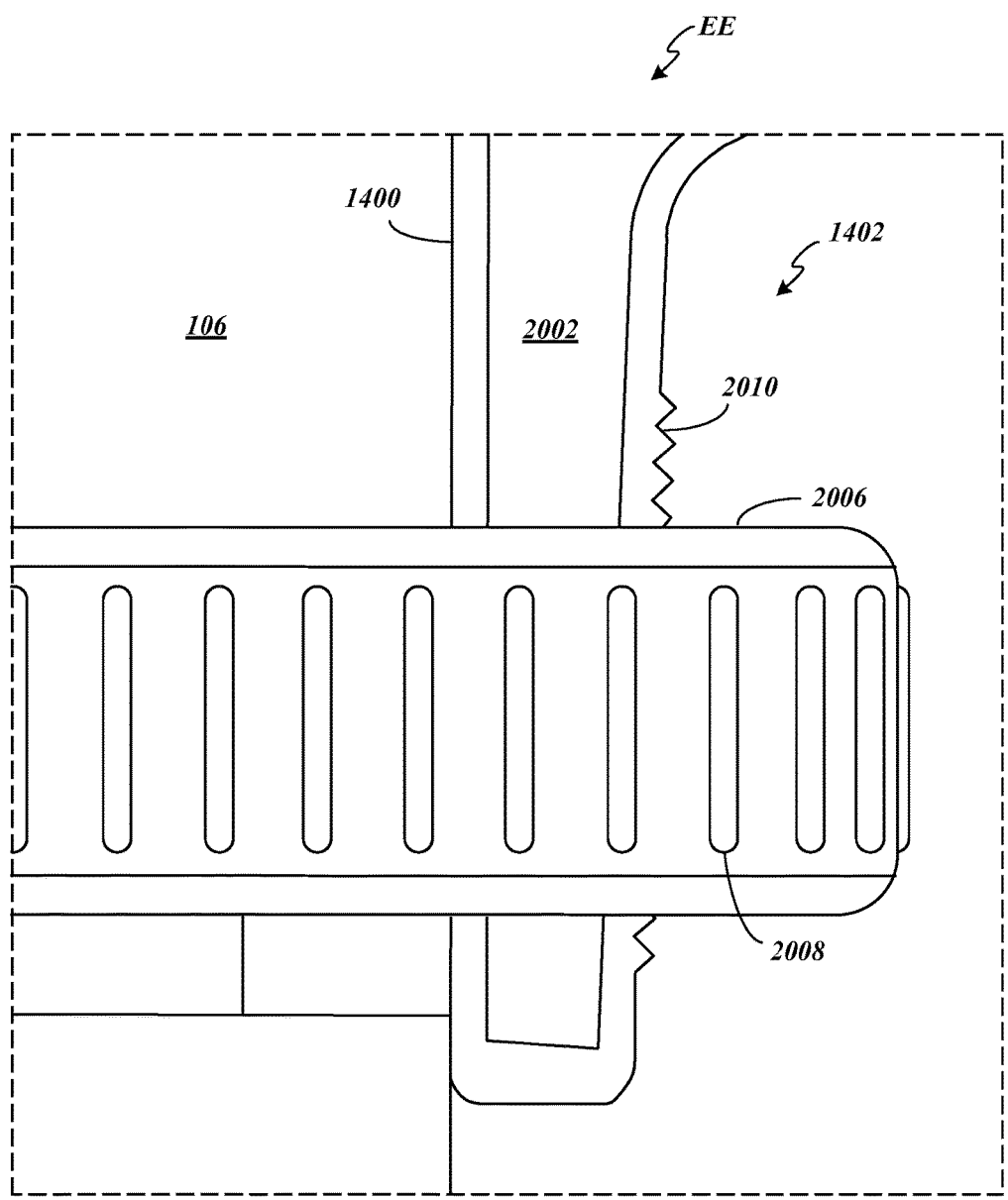
FIG. 20 depicts a magnified view of the portion surrounded by dashed lines and labeled EE in FIG. 18A.

FIG. 20 depicts details of the compression fitting 1402 for securing the lower case 1400 to the housing 106 of the medication delivery device 100 by illustrating a magnified view of the area surrounded by the dashed lines labeled EE in FIG. 18A. A flexible, hollow, threaded cone 2002 is provided at the base of the lower case 1400 including a gap (not shown in FIG. 18A or 20 but see 1406 of FIG. 14). The threaded cone 2002 is placed around the housing 106 of the medication delivery device 100 and a compression nut 2006 including ridges 2008 for grip is screwed onto the threaded cone 2002. As the threaded cone 2002 extends up along the lower case 1400, the threads 2010 increase in diameter and in response to the compression nut 2006 being tightened, the threaded cone 2002 is compressed and constricted around the housing 106, securing the lower case 1400 to the housing 106 of the medication delivery device 100. In some embodiments, the lower case 1400 including the threaded cone 2002 is made from a semi-flexible material such as aluminum or hard plastic and the compression nut 2006 is made from nylon or hard plastic. Many other practicable materials can be used for these components.

Figure 21:
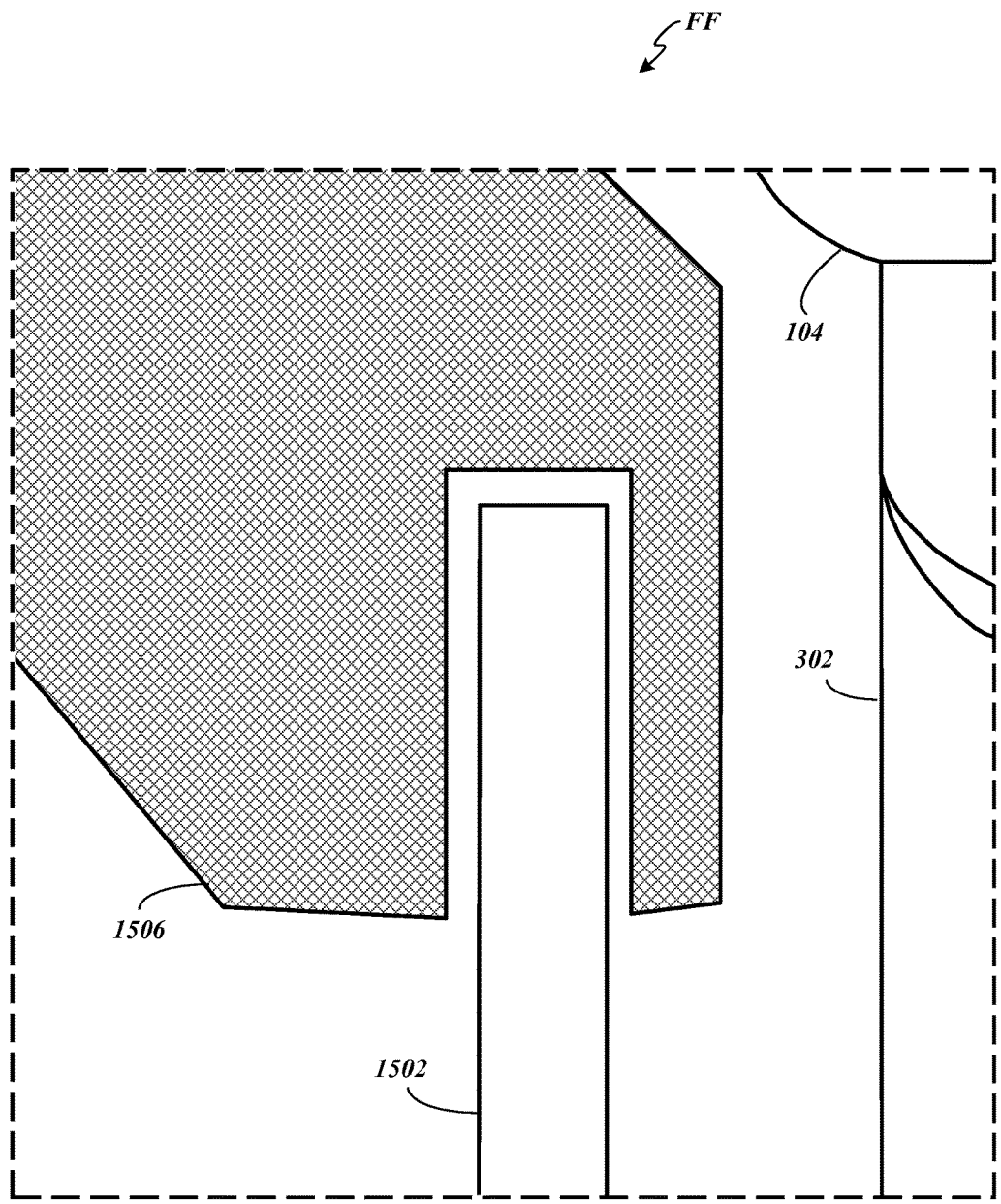
FIG. 21 depicts a magnified view of the portion surrounded by dashed lines and labeled FF in FIG. 18A.

FIG. 21 depicts a magnified view of a portion of the knob cover 1506 surrounded by dashed lines and labeled FF in FIG. 18A. In particular, this detail illustrates that cylinder shaft 1502 is attached to the knob cover 1506. Thus, since knob cover 1506 is coupled to the dose knob 104 via gasket 1814, cylinder shaft 1502 is linked to the dose knob 104.

Figure 22:
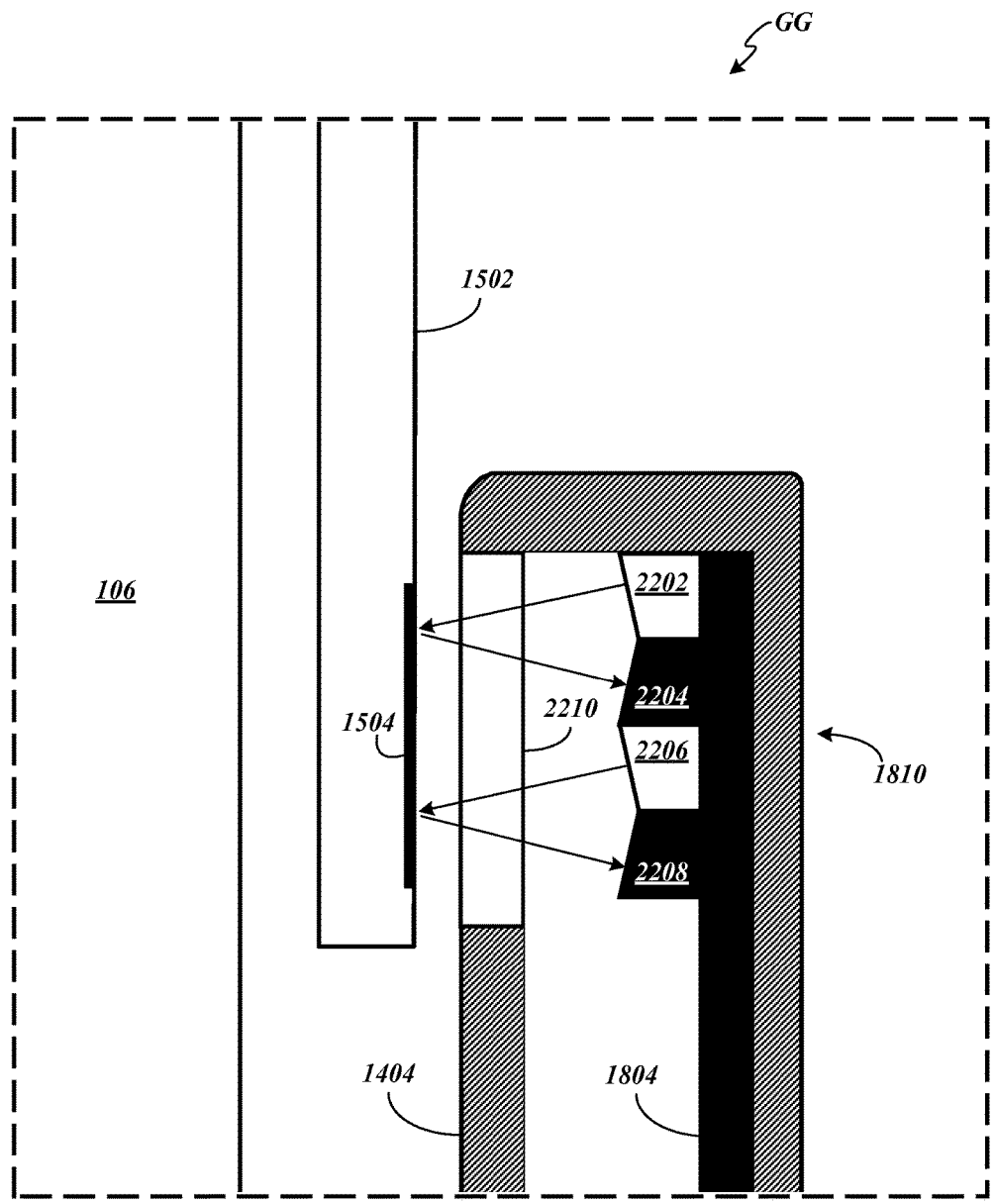
FIG. 22 depicts a magnified view of the portion surrounded by dashed lines and labeled GG in FIG. 18A.

FIG. 22 depicts a magnified view of a portion of the electronic circuit 1804 surrounded by dashed lines and labeled GG in FIG. 18A. In particular, this detail illustrates the sensor assembly 1810 which is part of the electronic circuit 1804. In some embodiments, the sensor assembly 1810 can include one or more emitter/detector pairs 2202/2204, 2206/2208 mounted on the circuit board of the electronic circuit 1804 and disposed so as to generally face the outer surface of the cylinder shaft 1502 and in particular, the dosage indicator markings 1504 (e.g., the spiral bar code strip) on the cylinder shaft 1502 through a sensor window 2210 in the lower casing 1404.

Figure 23:
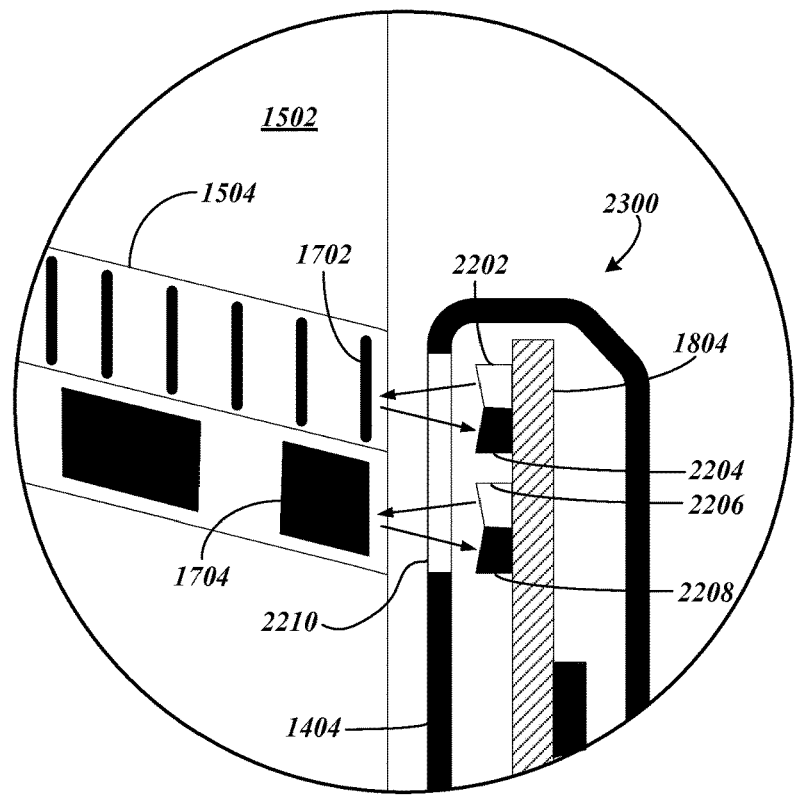
FIG. 23 depicts an example of a sensor assembly according to some embodiments of the present invention.

FIG. 23 depicts an example of an optical sensor assembly 2300 according to some embodiments of the present invention. In this embodiment, two emitter/detector pairs 2202/2204, 2206/2208 are mounted on the circuit board of the electronic circuit 1804 and disposed so as to face the dosage indicator markings 1504 (e.g., the spiral bar code strip) on the cylinder shaft 1502 through a sensor window 2210 in the body portion 1404 of the lower casing 1400. The upper emitter/detector pair 2202/2204 is disposed to align with the upper set of indicators 1702 which can be used for synchronization and dose knob position tracking. These indicator marks are spaced to correspond to the dose markings 304 on the medication delivery device's dose stem 302 (FIG. 3B). The lower emitter/detector pair 2206/2208 is disposed to align with the second set of indicators 1704 at the lower portion of the spiral dosage indicator markings 1504. These indicators 1704 can be read to determine an identifier code for medication type (e.g., insulin type).

In operation, the optical sensor assembly 2300 reads the dosage indicator markings 1504 (e.g., the spiral bar code strip) created with printed marks having a high contrast relative to the background. An LED can be used as an emitter to shine light on the dosage indicator markings 1504 and a light detector can sense the reflection of the light from the dosage indicator markings 1504. The light sensor assembly 2300 detects changing reflection levels each time one of the indicator marks 1702 passes by the sensor window 2210. Each indicator mark 1702 represents one tick and corresponds to a fixed volume of medication being set for dosing. Thus, when the dose knob 104 is being rotated by turning the knob cover 1506, the sensor assembly 2300 reads synchronization/position indicator marks 1702. The number of indicator marks 1702 is proportional to the angle of dose knob rotation and is proportional to selected medication dose. Concurrently, a medication type code can be read from the lower portion of the dosage indicator markings 1504. The length of each indicator mark 1704 can be interpreted as a digital numeric value as described below with respect to the timing diagrams of FIG. 25.

Figure 24:
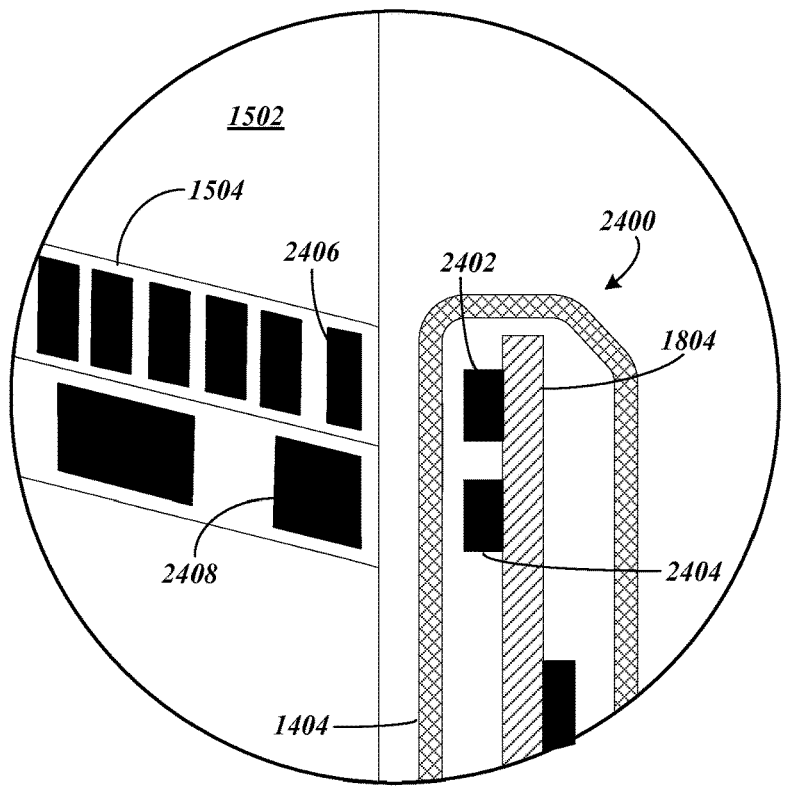
FIG. 24 depicts an alternative example of a sensor assembly according to some embodiments of the present invention.

FIG. 24 depicts an alternative example of a magnetic or capacitive sensor assembly 2400 according to some embodiments of the present invention. In this embodiment, two magnetic or capacitive sensors 2402, 2404 are mounted on the circuit board of the electronic circuit 1804 and disposed so as to face the dosage indicator markings 1504 (e.g., the spiral bar code strip) on the cylinder shaft 1502 through the body portion 1404 of the lower casing 1400. Note that an aperture or window is not required since the material used for the body portion 1404 is transparent to electric and magnetic fields. The upper magnetic or capacitive sensor 2402 is disposed to align with an upper set of metallic indicators 2406 which can be used for synchronization and dose knob position tracking. Note that in this embodiment, metallic indicators 2406, 2408 are used in place of dark markings so that the magnetic or capacitive sensors 2402, 2406 can detect the indicators 2406, 2408. These indicator marks are spaced to correspond to the dose markings 304 on the medication delivery device's dose stem 302 (FIG. 3B). The lower magnetic or capacitive sensor 2404 is disposed to align with a second set of metallic indicators 2408 at the lower portion of the spiral dosage indicator markings 1504. These indicators 2408 can be read to determine an identifier code for medication type (e.g., insulin type).

In operation, a magnetic sensor assembly and a capacitive sensor assembly both function in a similar manner. Rather than using optically sensed marks that have contrasting light reflectivity with the area between the marks, metalized pads are printed or affixed as the dosage indicator markings 1504 on the cylinder shaft 1502. The presence of a metalized pad changes the capacitance detected by the capacitive sensor. As the cylinder shaft 1502 rotates past each metallized pad, a tick is counted corresponding to a fixed volume of medication being set for dosing.

In some embodiments, a magnetic sensor assembly can be used to read the indicator markings 1504 on the cylinder shaft 1502. A magnetic sensor assembly can use a multi-pole ring magnet with alternating North and South polarities. As the cylinder shaft 1502 rotates about the medication delivery device, a Hall Effect sensor detects the changing polarities. Each polarity change represents one tick and corresponds to a fixed volume of medication being set for dosing.

Figure 25:
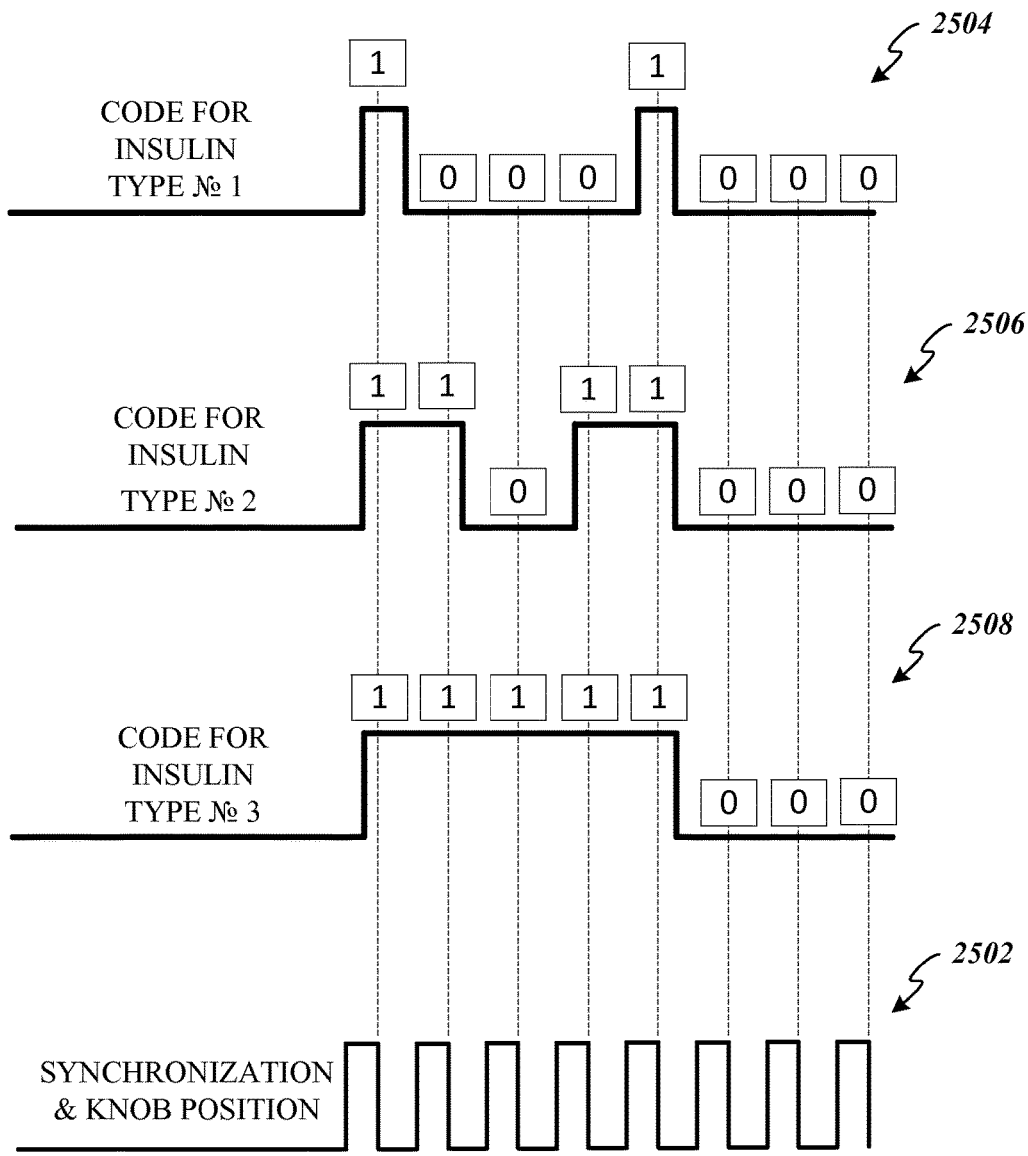
FIG. 25 depicts examples of timing diagrams according to some embodiments of the present invention.

FIG. 25 depicts examples of timing diagrams for interpreting the dosage indicator markings 1504 (e.g., the spiral bar code strip) on the cylinder shaft 1502 according to some embodiments of the present invention. These examples are applicable to any type of sensor (e.g., optical, magnetic, capacitive, etc.) used. The synchronization and knob position timing diagram 2502 is generated from sensing the upper indicators 1702, 2406 of the dosage indicator markings 1504 on the cylinder shaft 1502. This timing diagram 2502 provides a synchronization clock signal by which the signals from the lower indicators 1704, 2408 are examined. In other words, on each falling edge of the synchronization and knob position timing diagram 2502, the value of the signal from the lower indicators 1704, 2408 is read. In FIG. 25, the dashed vertical lines that are projected up to the three example timing diagrams 2504, 2506, 2508 from the falling edges of the synchronization and knob position timing diagram 2502, reflect that the values of the signals plotted in the other timing diagrams 2504, 2506, 2508 are evaluated at points in time corresponding to the falling edges of the synchronization and knob position timing diagram 2502.

Thus, the numeric value of the first (i.e., top most) example timing diagram 2504 is an eight bit binary code for insulin type no. 1 and is "10001000" which is "136" in decimal. The numeric value of the second (i.e., middle) example timing diagram 2506 is an eight bit binary code for insulin type no. 2 and is "11011000" which is "216" in decimal. The numeric value of the third (i.e., bottom most) example timing diagram 2508 is an eight bit binary code for insulin type no. 3 and is "11111000" which is "248" in decimal.

Figure 26A:
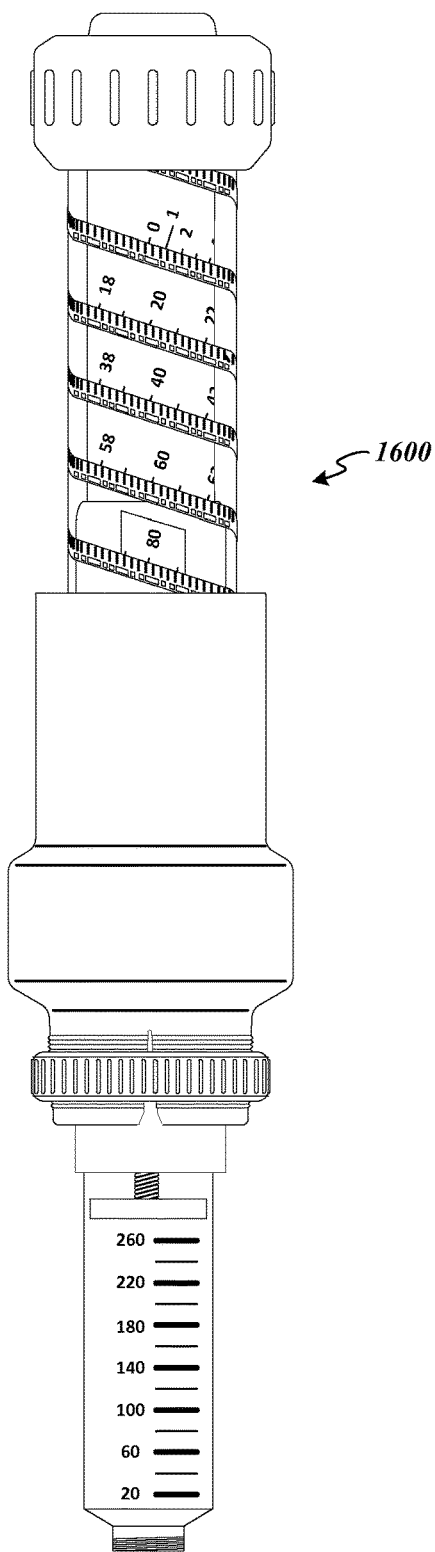
FIG. 26A depicts a view of an example embodiment of a fully assembled automated dose monitoring apparatus in the extended position and coupled to the medication delivery device of FIG. 1 according to some embodiments of the present invention.
Figure 26B:
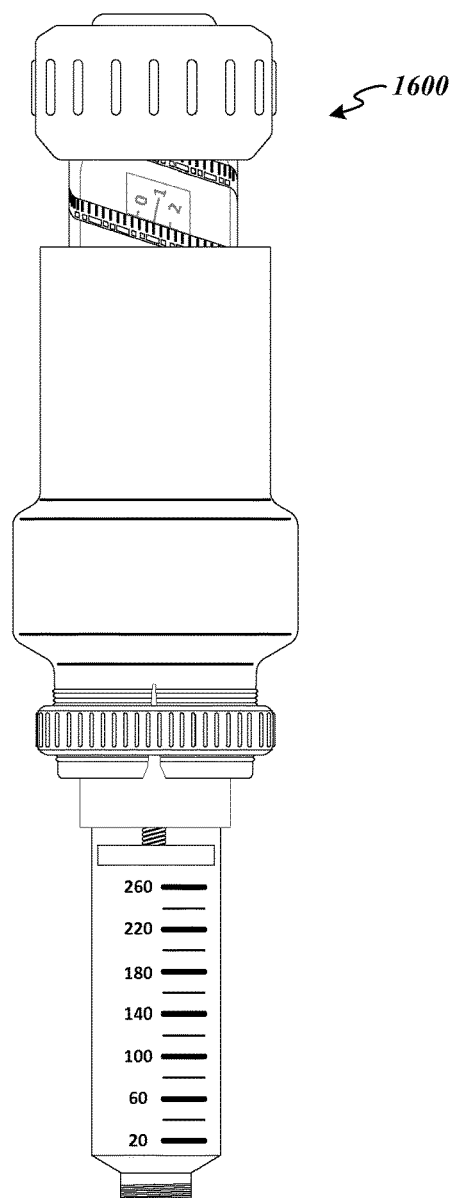
FIG. 26B depicts a view of an example embodiment of a fully assembled automated dose monitoring apparatus in the retracted position and is coupled to the medication delivery device of FIG. 1 according to some embodiments of the present invention.

FIG. 26A depicts a view of an example embodiment of a fully assembled automated dose monitoring apparatus 1600 in the extended position and coupled to the medication delivery device 100 of FIG. 1. FIG. 26B depicts a view of an example embodiment of a fully assembled automated dose monitoring apparatus in the retracted position and is coupled to the medication delivery device 100 of FIG. 1. The automated dose monitoring apparatus 1600 in FIG. 26A is engaged and ready to be used to inject an 80 unit dose of medication (assuming a needle is attached). The automated dose monitoring apparatus 1600 in FIG. 26B is disengaged.

Figure 27:
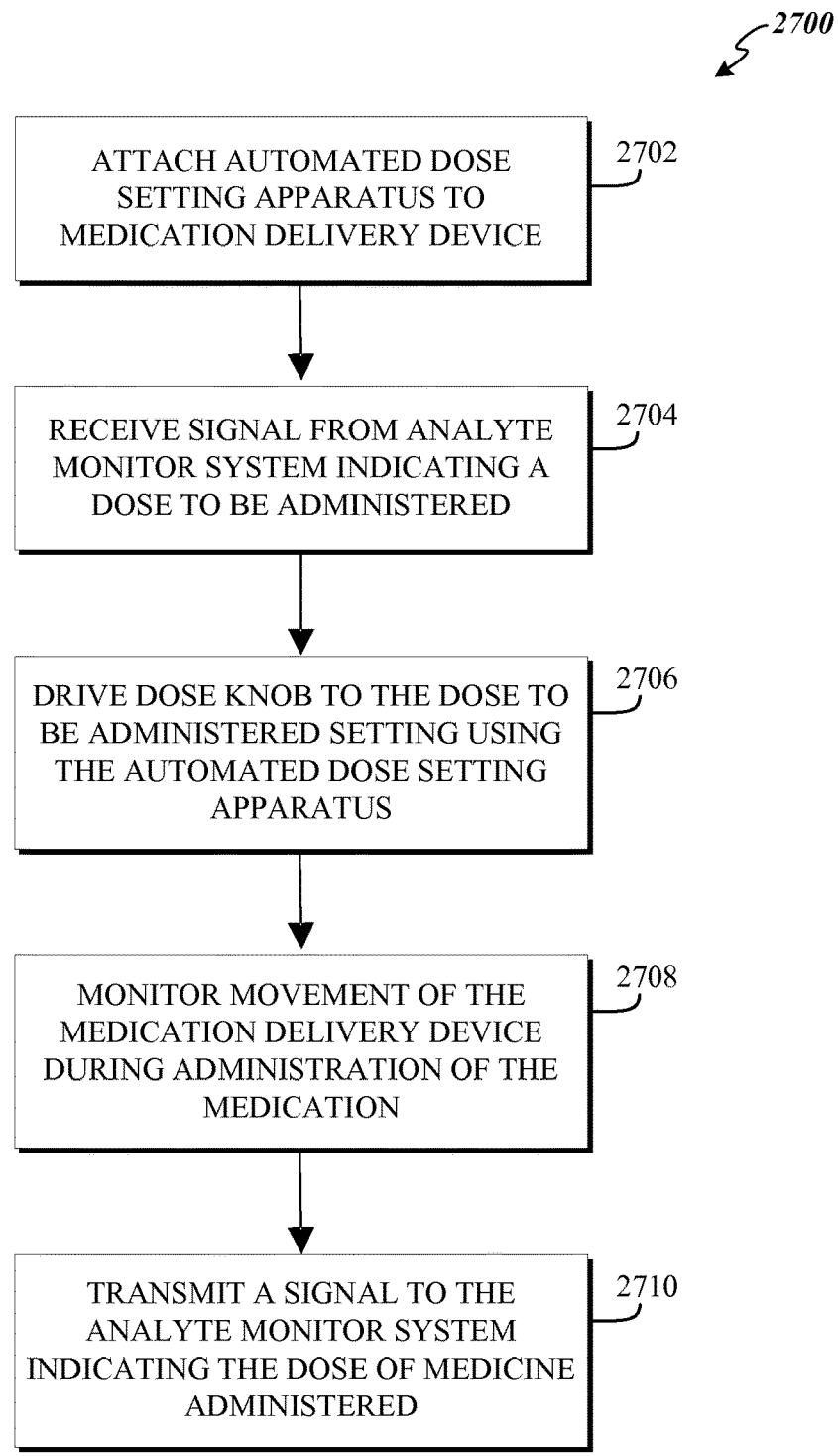
FIG. 27 depicts a flowchart representing an example method according to some embodiment of the present invention.

Turning now to FIG. 27, a flow chart depicting an example method 2700 according to some embodiments of the present invention is provided. Initially, the automated dose setting apparatus 1300 is attached to a medication delivery device 100 (2702). A signal from an analyte monitoring system or other health data management device is transmitted to the automated dose setting apparatus 1300 (2704). The signal includes information indicating an appropriate dose of medication to be administered. The automated dose setting apparatus 1300 drives the dose knob of the medication delivery device 100 to a setting corresponding to the received dose to be administered (2706). In some embodiments, the automated dose setting apparatus 1300 can monitor the setting of the dose to verify that the correct dose is actually set. In such embodiments, the automated dose setting apparatus 1300 can provide an indication that the correct dose is set or trigger an alarm if a dose different than the intended dose is set. In some embodiments, the indication and/or alarm can be via audible indicia and/or via a display.

In some embodiments, the automated dose setting apparatus 1300 can monitor the administration of the medication by monitoring movement of the medication delivery device 100 during administration of the medication (2708). In such embodiments, the automated dose setting apparatus 1300 can transmit a signal to the analyte monitoring system or other health data management device indicating the dose (and type) of medication that was administered (2710).

Figure 28:
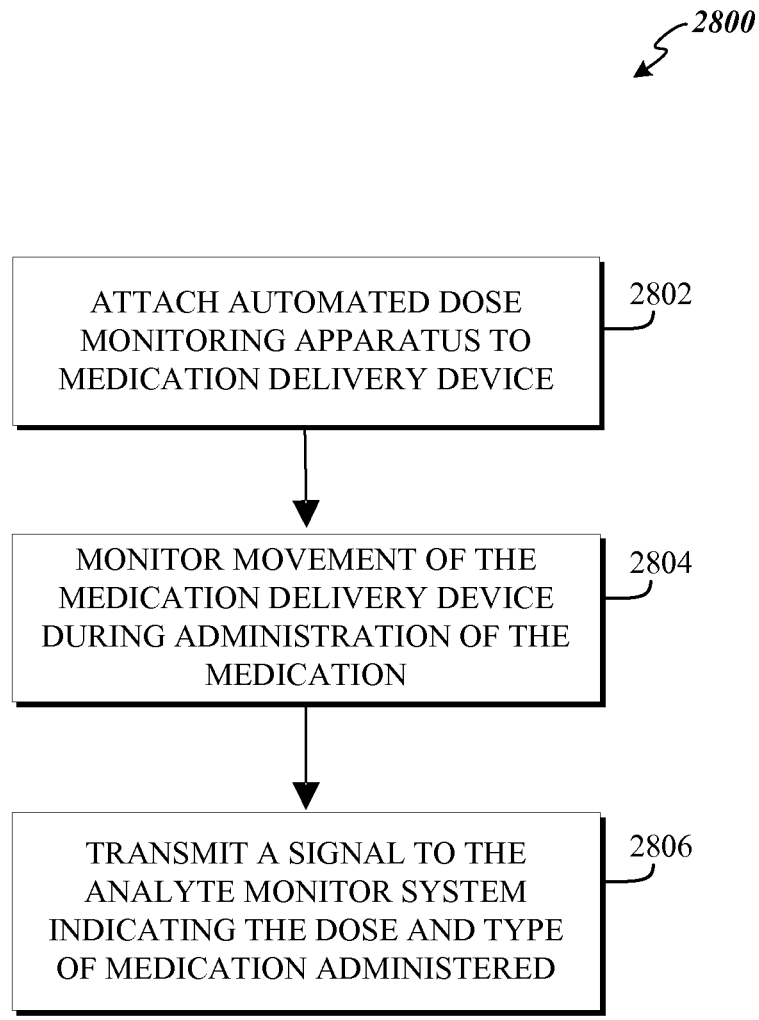
FIG. 28 depicts a flowchart representing an example alternative method according to some embodiment of the present invention.

Turning now to FIG. 28, a flow chart depicting an example method 2800 according to some embodiments of the present invention is provided. Initially, the automated dose monitoring apparatus 1600 is attached to a medication delivery device 100 (2802). Movement of the medication delivery device 100 is monitored by the automated dose monitoring apparatus 1600 during administration of the medication (2804). The automated dose monitoring apparatus 1600 transmits a signal to an analyte monitoring system or other health data management device indicating the dose (and type) of medication that was administered (2806) along with a time and date of the administration.

The foregoing description discloses only example embodiments of the invention. Modifications of the above-disclosed apparatus, systems and methods which fall within the scope of the invention will be readily apparent to those of ordinary skill in the art. Accordingly, while the present invention has been disclosed in connection with example embodiments, it should be understood that other embodiments may fall within the scope of the invention, as defined by the following claims.

The invention claimed is:

1. An apparatus, comprising:
    a first portion coupleable onto a top of a manually-operated dose knob of a medication delivery device; and
    a second portion coupled to the first portion and coupleable onto a top of a housing of the medication delivery device,
    wherein the second portion is operable to receive dose information electronically from an external device and to drive the first portion to operate the dose knob to set a dosage of the medication delivery device.

2. The apparatus of claim 1 further comprising an electronic circuit contained in the second portion and wherein the electronic circuit includes a controller, a driver assembly, and a transceiver.

3. The apparatus of claim 2 wherein the driver assembly includes two actuators operable to rotate the first portion.

4. The apparatus of claim 2 wherein the electronic circuit further includes a sensor assembly operable to detect rotation of the first portion.

5. The apparatus of claim 1 wherein the first portion includes a cylinder shaft having tooth fluting.

6. The apparatus of claim 5 wherein the second portion includes a driver assembly operable to rotate the cylinder shaft using alternating linear actuators.

7. The apparatus of claim 1 wherein the second portion includes a display operable to indicate a dosage setting of the medication delivery device.

8. A method, comprising:
    attaching an automated dose setting apparatus onto a top of a medication delivery device;
    receiving a first signal from an external analyte monitoring system, the first signal indicating a dose of medication to be administered; and
    driving a manually-operated dose knob of the medication delivery device with the automated dose setting apparatus to set a dose corresponding with the dose of medication to be administered.

9. The method of claim 8 further comprising:
    monitoring movement of the medication delivery device while the dose knob is driven by the automated dose setting apparatus; and
    verifying that the dose set by the automated dose setting apparatus corresponds with the dose of medication to be administered.

10. The method of claim 8 further comprising:
    monitoring movement of the medication delivery device while the medication is being administered; and
    verifying that a dose of medication actually administered corresponds with the dose of medication to be administered.

11. The method of claim 10 further comprising:
    providing an indication if the dose of medication actually administered corresponds with the dose of medication to be administered; and
    providing an alarm if the dose of medication actually administered does not correspond with the dose of medication to be administered.

12. The method of claim 8 further comprising:
    transmitting a second signal to the analyte monitoring system from the automated dose setting apparatus, the second signal indicating a dose of medication actually administered.

13. The method of claim 8 wherein attaching an automated dose setting apparatus to a medication delivery device includes coupling a first portion of the automated dose setting apparatus to the dose knob of the medication delivery device.

14. The method of claim 8 wherein attaching an automated dose setting apparatus to a medication delivery device includes coupling a second portion of the automated dose setting apparatus to a housing of the medication delivery device.

15. The method of claim 8 wherein driving a dose knob of the medication delivery device includes rotating a first portion of the automated dose setting apparatus coupled to the dose knob by driving the first portion using a driver assembly in a second portion of the automated dose setting apparatus that is coupled to a housing of the medication delivery device.

16. The method of claim 15 wherein driving the first portion using a driver assembly in the second portion of the automated dose setting apparatus includes rotating the first portion using alternating linear actuators.

17. An apparatus, comprising:
a first portion coupleable onto a top of a manually-operated dose knob of a medication delivery device, the first portion movable to operate the dose knob; and
a second portion coupled to the first portion and coupleable onto a top of a housing of the medication delivery device,
wherein the second portion is operable to monitor movement of the first portion and to transmit a signal electronically to an external device indicative of a dose of medication administered with the medication delivery device.

18. The apparatus of claim 17 wherein the first portion includes a transparent cylinder shaft operable to surround a dose stem of the medication delivery device.

19. The apparatus of claim 18 wherein the cylinder shaft includes at least one set of dosage indicator markings detectable by a sensor assembly within the second portion.

20. The apparatus of claim 17 wherein the first portion is rotatably coupleable to the second portion.

* * * * *